United States Patent
Miao et al.

(10) Patent No.: US 10,213,347 B2
(45) Date of Patent: Feb. 26, 2019

(54) ABSORBENT ARTICLE WITH AN APERTURED MULTI-LAYERED TOPSHEET

(71) Applicant: Kimberly-Clark Worldwide, Inc., Neenah, WI (US)

(72) Inventors: Lin Miao, Beijing (CN); Xueen George Hao, Beijing (CN); Chun Lei Pu, Beijing (CN)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 800 days.

(21) Appl. No.: 14/646,398

(22) PCT Filed: Dec. 4, 2012

(86) PCT No.: PCT/CN2012/085812
§ 371 (c)(1),
(2) Date: May 21, 2015

(87) PCT Pub. No.: WO2014/085974
PCT Pub. Date: Jun. 12, 2014

(65) Prior Publication Data
US 2015/0313766 A1 Nov. 5, 2015

(51) Int. Cl.
*A61F 13/475* (2006.01)
*A61F 13/511* (2006.01)
(Continued)

(52) U.S. Cl.
CPC .......... *A61F 13/475* (2013.01); *A61F 13/512* (2013.01); *A61F 13/513* (2013.01);
(Continued)

(58) Field of Classification Search
CPC ............... A61F 13/472; A61F 13/4756; A61F 13/51104; A61F 13/5116; A61F 13/512;
(Continued)

(56) References Cited

U.S. PATENT DOCUMENTS 2,566,451 A 9/1951 Julien
2,575,165 A 11/1951 Donovan
(Continued)

FOREIGN PATENT DOCUMENTS

EP 0 343 941 B1 11/1989
EP 0 619 726 B1 4/1997
(Continued)

OTHER PUBLICATIONS

Abstract of Chinese Design Patent—CN201410036Y, Feb. 24, 2010, 1 page.
(Continued)

*Primary Examiner* — Kathryn E Ditmer
(74) *Attorney, Agent, or Firm* — Dority & Manning, P.A.

(57) ABSTRACT

An absorbent article (100-1200) is capable of providing comfort to the wearer and can maintain dryness and inhibit the leakage of fluid. The absorbent article (100-1200) includes a multi-layered topsheet (138). The multi-layered topsheet (138) includes a first topsheet layer (106) having an opening (148) and a second topsheet layer (108) disposed under the first topsheet layer (106). The first topsheet layer (106) and the second topsheet layer (108) are joined together by a seal that, in one embodiment, generally corresponds with the shape of the opening (148). Further, a first sub-topsheet layer (116) is situated beneath the multi-layered topsheet (138) and has an opening (150) that is smaller than the first topsheet layer opening (148). This combination of openings (148, 150) situated one below the other provides for an absorbent article (100-1200) that can maintain a high level of dryness and its ability to conform to the wearer's body, and inhibit the leakage of bodily fluids due to a funnel-like effect.

26 Claims, 23 Drawing Sheets

(51) Int. Cl.
*A61F 13/512* (2006.01)
*A61F 13/513* (2006.01)
*A61F 13/51* (2006.01)

(52) U.S. Cl.
CPC ...... *A61F 13/5116* (2013.01); *A61F 13/5125* (2013.01); *A61F 13/51104* (2013.01); *A61F 2013/5127* (2013.01); *A61F 2013/51078* (2013.01); *A61F 2013/51092* (2013.01); *A61F 2013/51186* (2013.01)

(58) Field of Classification Search
CPC .............. A61F 13/5123; A61F 13/5125; A61F 13/51394; A61F 2013/5128; A61F 2013/51383
See application file for complete search history.

(56) References Cited

U.S. PATENT DOCUMENTS

| | | |
|---|---|---|
| 3,073,309 A | 1/1963 | Mosier |
| 3,343,543 A | 9/1967 | Glassman |
| 3,441,023 A | 4/1969 | Rijssenbeek |
| 3,545,441 A | 12/1970 | Gravdahl |
| 3,575,174 A * | 4/1971 | Mogor .............. A61F 13/47218 604/370 |
| 3,828,786 A | 8/1974 | Cervantes |
| 3,881,490 A | 5/1975 | Whitehead et al. |
| 3,889,679 A | 6/1975 | Taylor |
| 3,913,580 A | 10/1975 | Ginocchio |
| 4,184,498 A | 1/1980 | Franco |
| 4,285,342 A | 8/1981 | Mesek |
| 4,337,772 A | 7/1982 | Roeder |
| 4,375,448 A | 3/1983 | Appel et al. |
| 4,376,799 A | 3/1983 | Tusim |
| 4,397,644 A | 8/1983 | Matthews et al. |
| 4,494,278 A | 1/1985 | Kroyer et al. |
| 4,501,586 A | 2/1985 | Holtman |
| 4,531,945 A | 7/1985 | Allison |
| 4,556,146 A | 12/1985 | Swanson et al. |
| 4,578,069 A | 3/1986 | Whitehead et al. |
| 4,610,678 A | 9/1986 | Weisman et al. |
| 4,624,666 A | 11/1986 | DeRossett et al. |
| 4,629,643 A | 12/1986 | Curro et al. |
| 4,631,062 A | 12/1986 | Lassen et al. |
| 4,640,810 A | 2/1987 | Laursen et al. |
| 4,662,876 A | 5/1987 | Wiegner |
| 4,673,403 A | 6/1987 | Lassen et al. |
| 4,731,065 A | 3/1988 | Yamada |
| 4,781,710 A | 11/1988 | Megison et al. |
| 4,795,455 A | 1/1989 | Luceri et al. |
| 4,935,022 A | 6/1990 | Lash et al. |
| 4,988,344 A | 1/1991 | Reising et al. |
| 4,988,345 A | 1/1991 | Reising |
| 5,176,672 A | 1/1993 | Bruemmer et al. |
| 5,188,625 A | 2/1993 | Van Iten et al. |
| 5,252,619 A | 10/1993 | Brownscombe et al. |
| 5,304,161 A * | 4/1994 | Noel ................. A61F 13/15203 604/358 |
| 5,348,547 A | 9/1994 | Payne et al. |
| H1377 H | 11/1994 | Perry |
| 5,364,382 A | 11/1994 | Latimer et al. |
| 5,366,451 A | 11/1994 | Levesque |
| 5,382,400 A | 1/1995 | Pike et al. |
| 5,397,316 A | 3/1995 | LaVon et al. |
| 5,415,640 A | 5/1995 | Kirby et al. |
| 5,429,632 A | 7/1995 | Tanji et al. |
| 5,439,458 A | 8/1995 | Noel et al. |
| 5,462,537 A | 10/1995 | Carr et al. |
| 5,527,171 A | 6/1996 | Soerensen |
| 5,533,991 A | 7/1996 | Kirby et al. |
| 5,580,418 A | 12/1996 | Alikhan |
| 5,662,633 A | 9/1997 | Doak et al. |
| 5,669,798 A | 9/1997 | Koczab |
| 5,692,939 A | 12/1997 | DesMarais |
| 5,695,849 A | 12/1997 | Shawver et al. |
| 5,743,896 A | 4/1998 | Parker |
| 5,755,710 A * | 5/1998 | Menard ............ A61F 13/15585 604/378 |
| 5,795,344 A | 8/1998 | Chappell |
| 5,810,798 A | 9/1998 | Finch |
| 5,820,619 A | 10/1998 | Chen |
| 5,830,203 A | 11/1998 | Suzuki et al. |
| 5,843,063 A | 12/1998 | Anderson et al. |
| 5,855,719 A | 1/1999 | Menard |
| 5,899,893 A | 5/1999 | Dyer et al. |
| 5,961,505 A | 10/1999 | Coe et al. |
| 5,990,375 A | 11/1999 | Lindquist et al. |
| 6,011,195 A | 1/2000 | Muhs et al. |
| 6,059,710 A | 5/2000 | Rajala et al. |
| 6,060,636 A | 5/2000 | Yahiaoui et al. |
| 6,074,333 A | 6/2000 | Rajala et al. |
| 6,075,179 A | 6/2000 | McCormack et al. |
| 6,077,254 A | 6/2000 | Silwanowicz et al. |
| 6,117,523 A | 9/2000 | Sugahara |
| 6,165,306 A | 12/2000 | Rajala |
| 6,171,432 B1 | 1/2001 | Brisebois et al. |
| 6,241,714 B1 | 6/2001 | Raidel et al. |
| D448,481 S | 9/2001 | Mok |
| 6,284,942 B1 | 9/2001 | Rabin |
| 6,376,095 B1 | 4/2002 | Cheung et al. |
| 6,395,792 B1 | 5/2002 | Nagasuna et al. |
| 6,410,823 B1 | 6/2002 | Daley et al. |
| 6,436,080 B1 | 8/2002 | Carlucci et al. |
| 6,461,339 B1 | 10/2002 | Sugahara |
| 6,548,732 B2 | 4/2003 | Erdman et al. |
| 6,573,424 B1 | 6/2003 | Raidel et al. |
| 6,610,903 B1 | 8/2003 | Latimer et al. |
| D483,485 S | 12/2003 | Phillips-Nicholas |
| 6,673,418 B1 | 1/2004 | DeOlivera et al. |
| 6,685,688 B2 | 2/2004 | Mishima et al. |
| 6,759,567 B2 | 7/2004 | Colman et al. |
| 6,786,893 B2 | 9/2004 | Strand |
| 6,811,239 B1 | 11/2004 | Salacz |
| 6,858,771 B2 | 2/2005 | Yoshimasa et al. |
| 6,911,574 B1 | 6/2005 | Mizutani |
| 6,913,599 B2 | 7/2005 | Mishima et al. |
| 6,984,225 B2 | 1/2006 | Raidel et al. |
| 7,037,298 B2 | 5/2006 | Ohshima et al. |
| 7,067,711 B2 | 6/2006 | Kuroda et al. |
| 7,145,054 B2 | 12/2006 | Zander et al. |
| 7,156,832 B2 | 1/2007 | Drevik et al. |
| 7,285,178 B2 | 10/2007 | Mischler et al. |
| 7,358,282 B2 | 4/2008 | Krueger et al. |
| 7,387,620 B2 | 6/2008 | Watanabe et al. |
| 7,388,123 B2 | 6/2008 | Cowell et al. |
| 7,402,157 B2 | 7/2008 | Christon et al. |
| 7,429,689 B2 | 9/2008 | Chen et al. |
| 7,442,188 B2 | 10/2008 | Franklin et al. |
| 7,462,755 B2 | 12/2008 | Toro et al. |
| D600,798 S | 9/2009 | Hood et al. |
| D600,799 S | 9/2009 | Hood et al. |
| D600,800 S | 9/2009 | Hood et al. |
| D600,802 S | 9/2009 | Hood et al. |
| D600,804 S | 9/2009 | Hood et al. |
| 7,594,905 B2 | 9/2009 | Tanio et al. |
| 7,597,690 B2 | 10/2009 | Tanio et al. |
| D612,491 S | 3/2010 | Sullivan Conrad et al. |
| 7,674,949 B2 | 3/2010 | Wahlstrom et al. |
| 7,686,790 B2 | 3/2010 | Rasmussen et al. |
| 7,718,844 B2 | 5/2010 | Olson |
| 7,736,688 B2 | 6/2010 | Oetjen et al. |
| 7,786,340 B2 | 8/2010 | Gagliardi et al. |
| 7,824,385 B2 | 11/2010 | Ecker et al. |
| D630,316 S | 1/2011 | Hood et al. |
| 7,927,320 B2 | 4/2011 | Goldwasser et al. |
| 7,976,523 B2 | 7/2011 | Suzuki et al. |
| 7,976,525 B2 | 7/2011 | McDaniel |
| 7,982,091 B2 | 7/2011 | Konawa |
| 8,016,803 B2 | 9/2011 | Mueller et al. |
| 8,039,685 B2 | 10/2011 | Mason, Jr. et al. |
| 8,142,876 B2 | 3/2012 | Ueminami et al. |
| 8,178,748 B2 | 5/2012 | Hammons et al. |
| 8,187,242 B1 | 5/2012 | Raidel et al. |

(56) References Cited

U.S. PATENT DOCUMENTS

| | | |
|---|---|---|
| 8,211,078 B2 | 7/2012 | Noel |
| 8,293,966 B2 | 10/2012 | Obele |
| 8,317,768 B2 | 11/2012 | Larsson |
| 8,536,401 B2 | 9/2013 | Ecker et al. |
| 8,541,644 B2 | 9/2013 | Raidel et al. |
| 8,754,286 B2 | 6/2014 | Bergström et al. |
| 8,764,719 B2 | 7/2014 | Bissah et al. |
| 8,915,898 B2 | 12/2014 | Dieringer et al. |
| 8,987,544 B2 | 3/2015 | Poruthoor et al. |
| 2001/0044610 A1 | 11/2001 | Kim et al. |
| 2003/0078553 A1 | 4/2003 | Wada et al. |
| 2003/0125701 A1 | 7/2003 | Widlund |
| 2003/0130643 A1 | 7/2003 | Drevik et al. |
| 2003/0153232 A1 | 8/2003 | Raidel et al. |
| 2003/0233080 A1 | 12/2003 | Backman et al. |
| 2004/0015145 A1* | 1/2004 | Miura ............ A61F 13/4755 604/367 |
| 2004/0133179 A1 | 7/2004 | Steger et al. |
| 2004/0170813 A1 | 9/2004 | Digiacomantonio et al. |
| 2006/0004333 A1* | 1/2006 | Olson ............... A61F 13/42 604/361 |
| 2006/0287635 A1 | 12/2006 | Angel, Jr. |
| 2007/0055210 A1 | 3/2007 | Kao |
| 2007/0073255 A1 | 3/2007 | Thomas et al. |
| 2007/0087169 A1 | 4/2007 | McFall |
| 2007/0135787 A1 | 6/2007 | Raidel et al. |
| 2008/0243100 A1 | 10/2008 | Wu et al. |
| 2010/0174260 A1 | 7/2010 | Di Luccio et al. |
| 2011/0106036 A1 | 5/2011 | Ståhl et al. |
| 2011/0137276 A1 | 6/2011 | Yoshikawa |
| 2012/0220972 A1 | 8/2012 | Kawamura et al. |
| 2012/0277711 A1 | 11/2012 | Kim et al. |
| 2013/0245589 A1 | 9/2013 | Toda et al. |
| 2013/0338621 A1 | 12/2013 | Ecker et al. |
| 2014/0128828 A1 | 5/2014 | Andersson et al. |
| 2014/0228795 A1 | 8/2014 | Castanares et al. |
| 2015/0094678 A1 | 4/2015 | O'Brien et al. |

FOREIGN PATENT DOCUMENTS

| | | | |
|---|---|---|---|
| EP | 0 769 284 A1 | 4/1997 | |
| EP | 1 301 156 B1 | 8/2006 | |
| EP | 1 842 513 A1 | 10/2007 | |
| EP | 1 842 512 B1 | 9/2011 | |
| EP | 1 196 122 B1 | 11/2011 | |
| FR | 2542608 A1 * | 9/1984 | ........... A61F 5/4401 |
| GB | 1349962 | 4/1974 | |
| GB | 1425179 | 2/1976 | |
| GB | 1595393 | 8/1981 | |
| GB | 2284767 | 6/1995 | |
| GB | 2283428 A | 10/1995 | |
| GB | 2370780 A | 7/2002 | |
| JP | S5985661 U | 5/1984 | |
| JP | H01122727 U | 8/1989 | |
| WO | WO 9109582 A1 | 7/1991 | |
| WO | WO 9211830 A2 | 7/1992 | |
| WO | WO 9701998 A1 | 1/1997 | |
| WO | WO 0037002 A1 | 6/2000 | |
| WO | WO 0069481 A1 | 11/2000 | |
| WO | WO 0069483 A1 | 11/2000 | |
| WO | WO 0069484 A1 | 11/2000 | |
| WO | WO 0069485 A1 | 11/2000 | |
| WO | WO 0069482 A1 | 12/2000 | |
| WO | WO 03015682 A1 | 2/2003 | |
| WO | WO 03015684 A1 | 2/2003 | |
| WO | WO 03086257 A1 | 10/2003 | |
| WO | WO 2006105305 A1 | 10/2006 | |
| WO | WO 2008146222 A1 | 12/2008 | |
| WO | WO 2009067059 A1 | 5/2009 | |
| WO | WO 2013002686 A1 | 1/2013 | |
| WO | WO 2013185800 A1 | 12/2013 | |

OTHER PUBLICATIONS

Abstract of Chinese Patent—CN1066776, Dec. 9, 1992, 2 page.
Abstract of Chinese Patent—CN201143260, Nov. 5, 2008, 1 page.
Abstract of Chinese Patent—CN202078469, Dec. 21, 2011, 1 page.
Abstract of Chinese Patent—CN102614049, Aug. 1, 2012, 1 page.
Abstract of European Patent—EP0119919, Sep. 26, 1984, 1 page.
Abstract of Japanese Patent—JP11042250, Feb. 16, 1999, 1 page.
Abstract of Japanese Patent—JP2004033325, Feb. 5, 2004, 2 pages.
Abstract of Japanese Patent—JP2006051211, Feb. 23, 2006, 2 pages.
Abstract of Japanese Patent—JP2006239162, Sep. 14, 2006, 2 pages.
Abstract of Japanese Patent—JP2007050145, Mar. 1, 2007, 1 page.
Abstract of Japanese Patent—JP2009112864, May 28, 2009, 1 page.
Abstract of South Korea Patent—KR0131762—Apr. 13, 1998, 2 pages.
Abstract and Machine Translation of Sweden Patent—SE520706, Aug. 12, 2003, 9 pages.
Machine Translation of European Patent—EP0164595, Dec. 18, 1985, 6 pages.
Machine Translation of French Patent—FR2420339, Oct. 19, 1979, 5 pages.
Machine Translation of JP Japanese Patent 6-21624, Jun. 3, 1994 6 pages.
Machine Translation of Japanese Patent—6-31722, Apr. 26, 1994, 10 pages.
Machine Translation of Japanese Patent—7-12119, Feb. 28, 1995, 11 pages.
Translation of Japanese Patent—JP59190229, Dec. 17, 1984, 5 pages.
Translation of Japanese Patent—JPH11076304 A2 Mar. 23, 1999, 8 pages.
International Search Report and Written Opinion for PCT/CN2012/085812 dated Sep. 12, 2013, 15 pages.

* cited by examiner

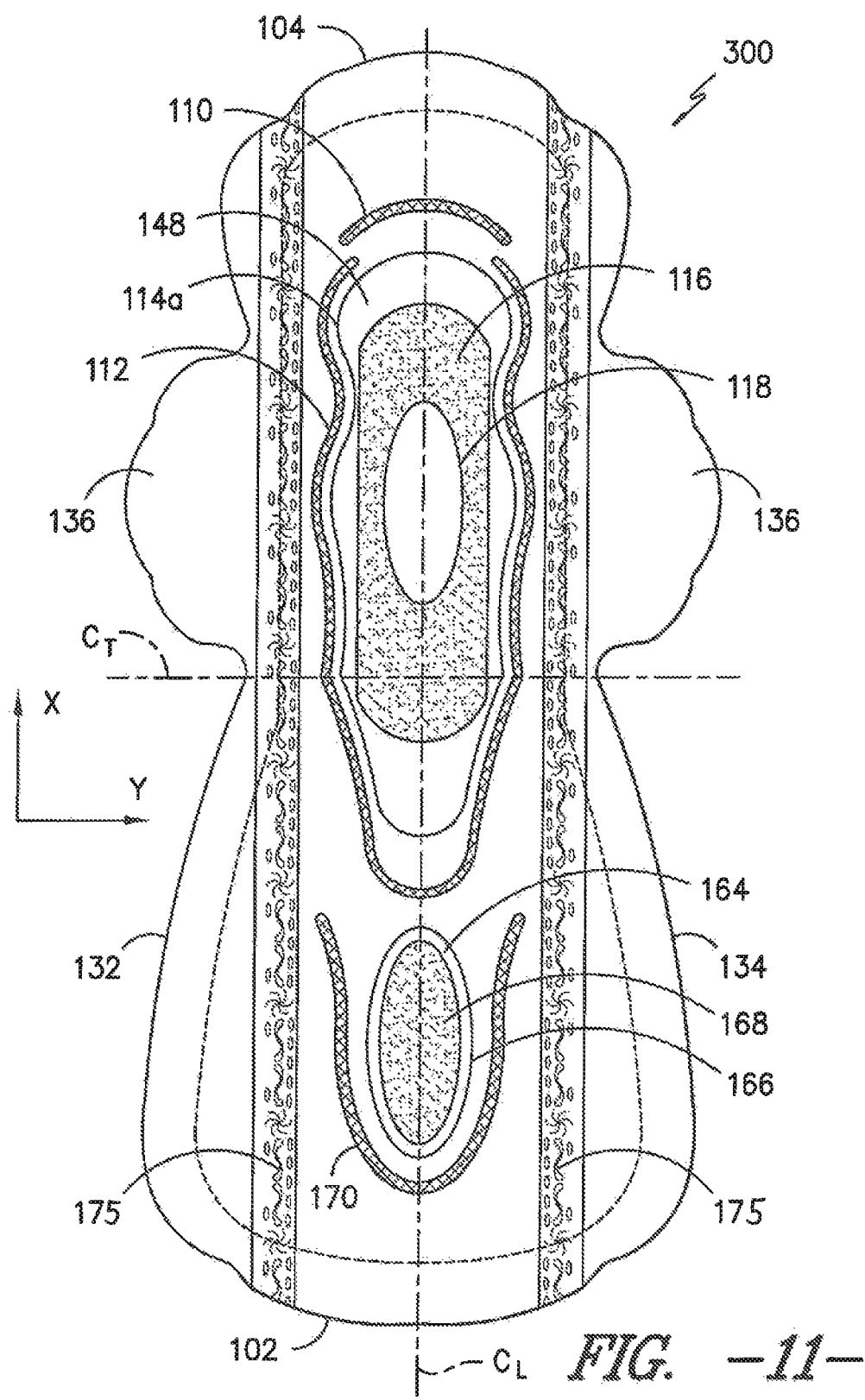
FIG. -11-

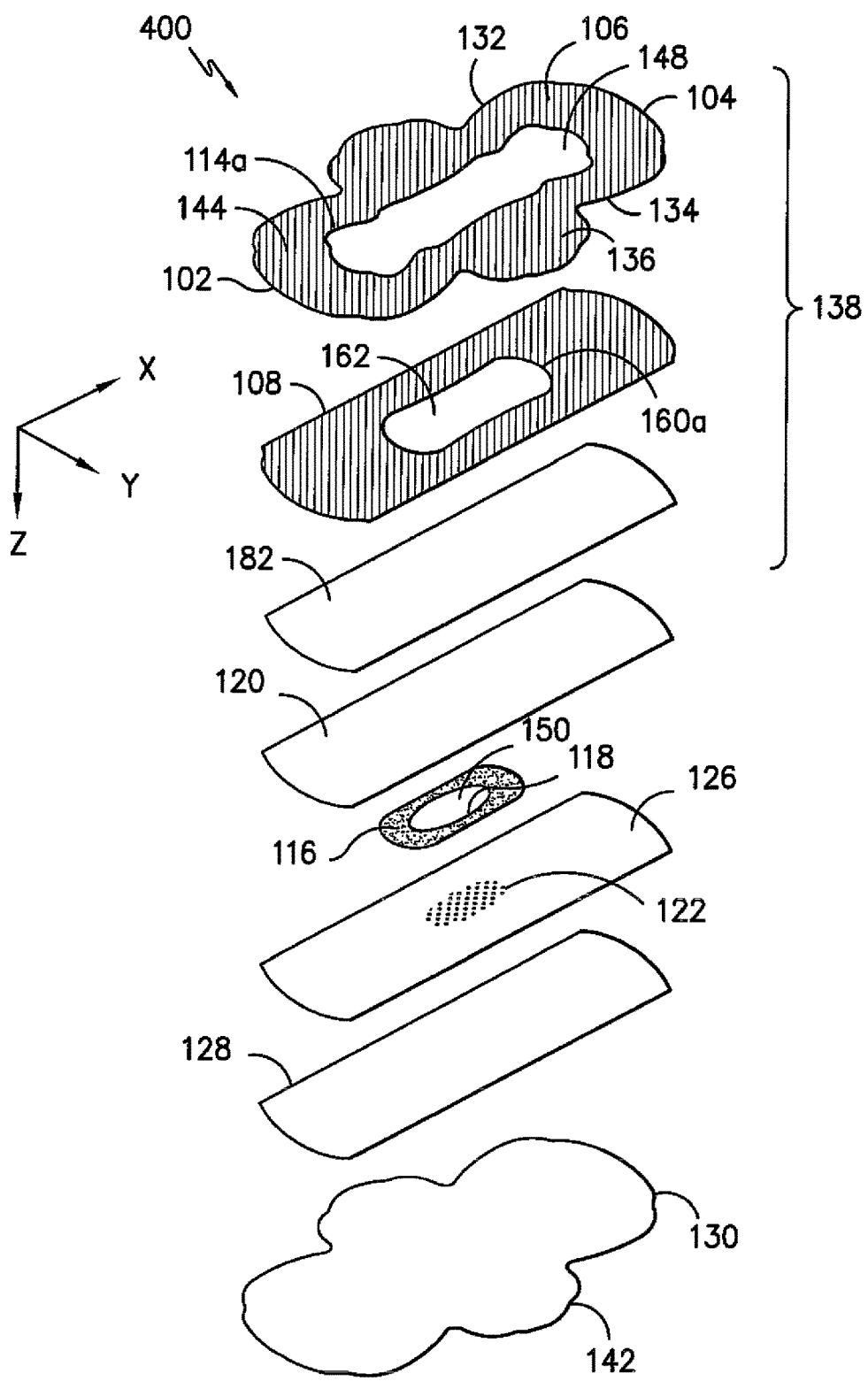
FIG. -12-

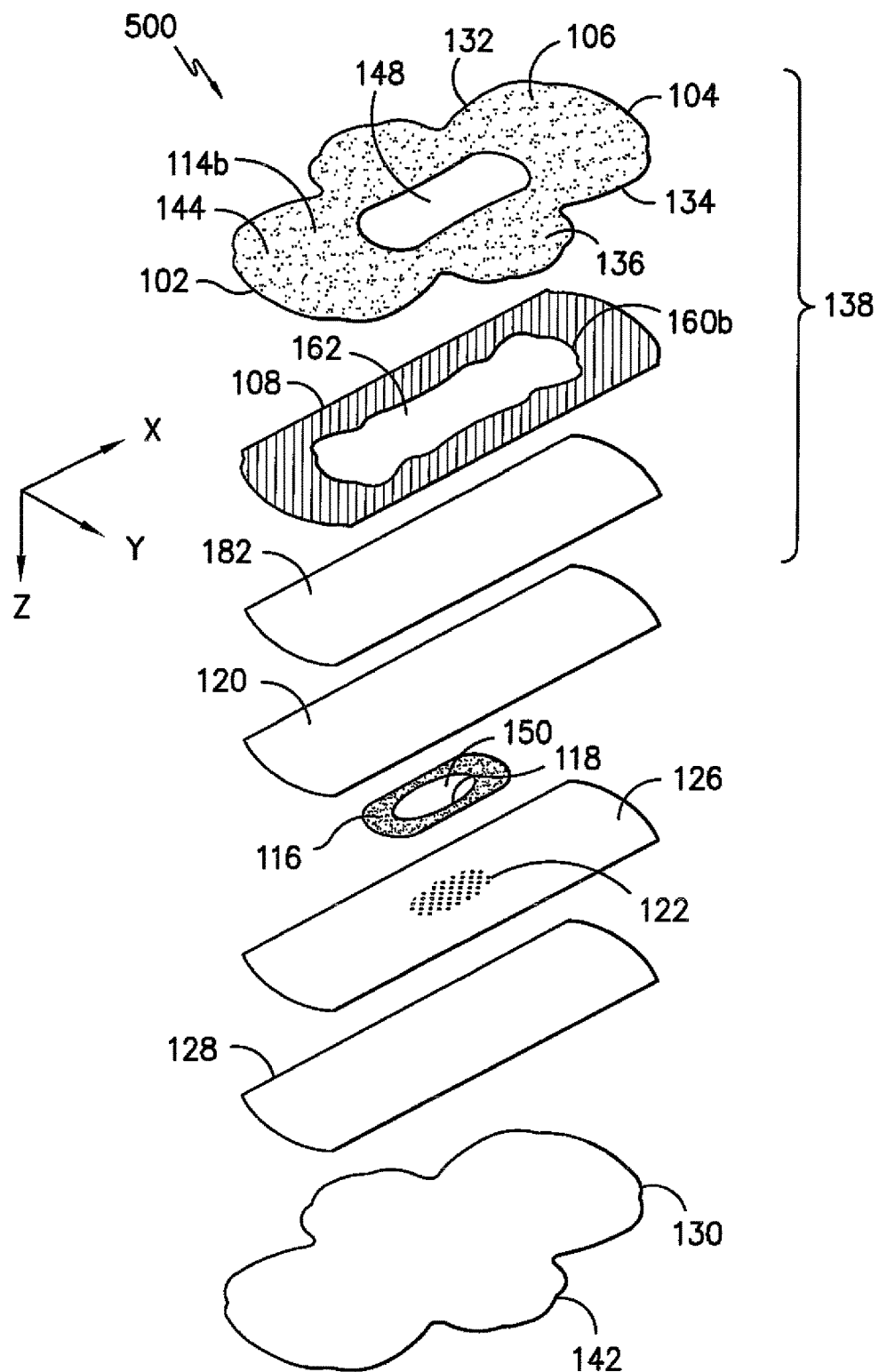
FIG. —13—

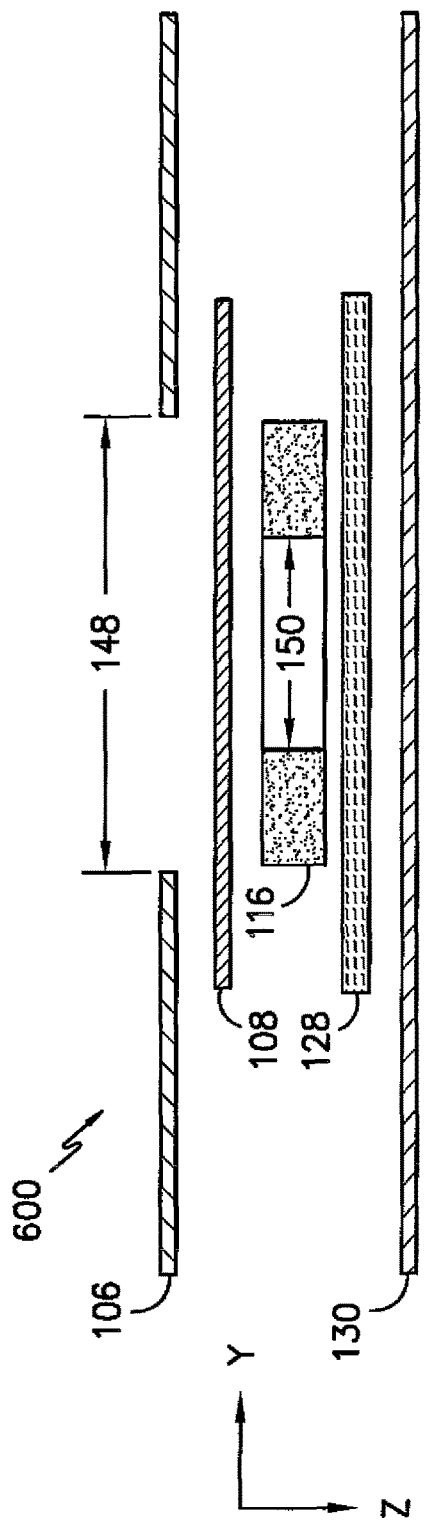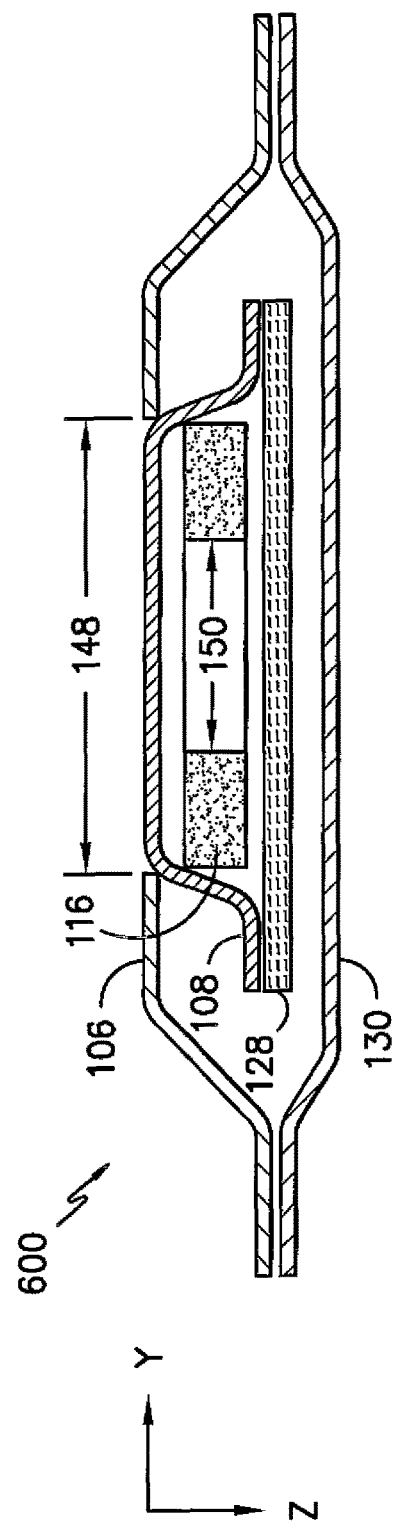

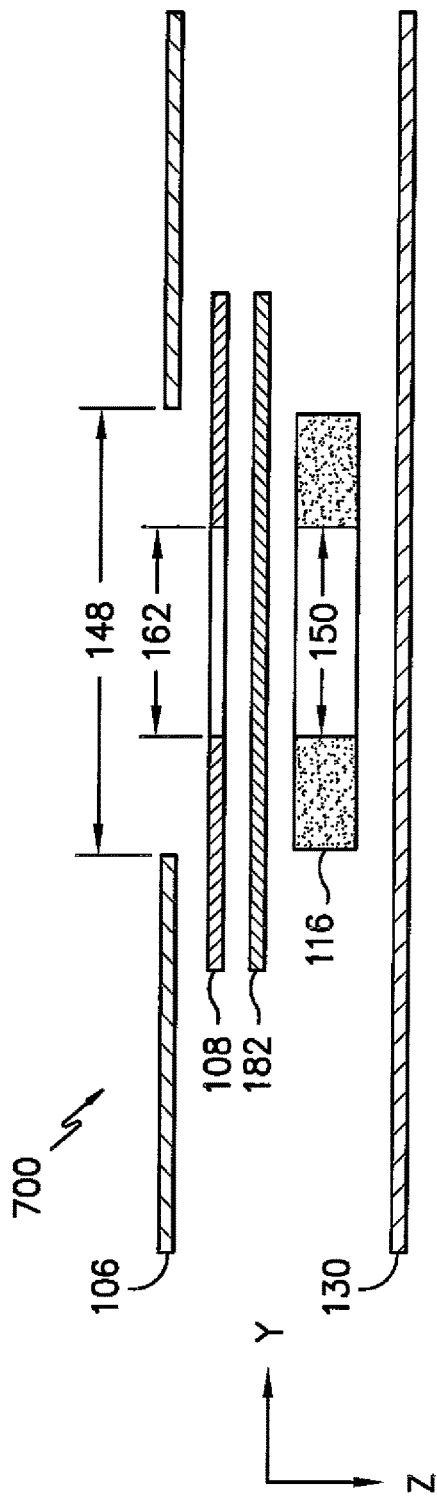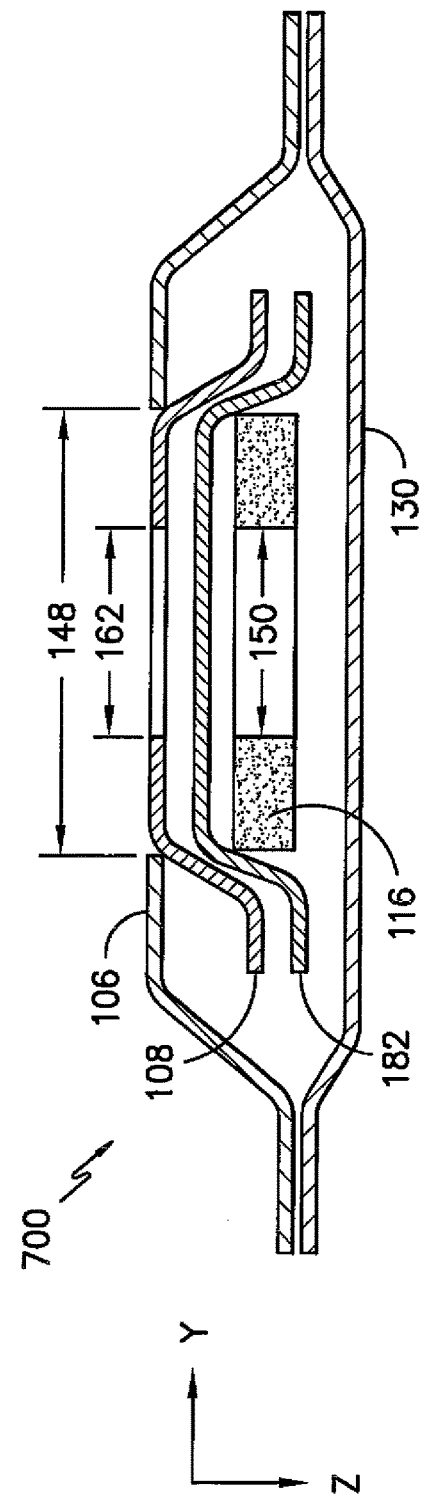

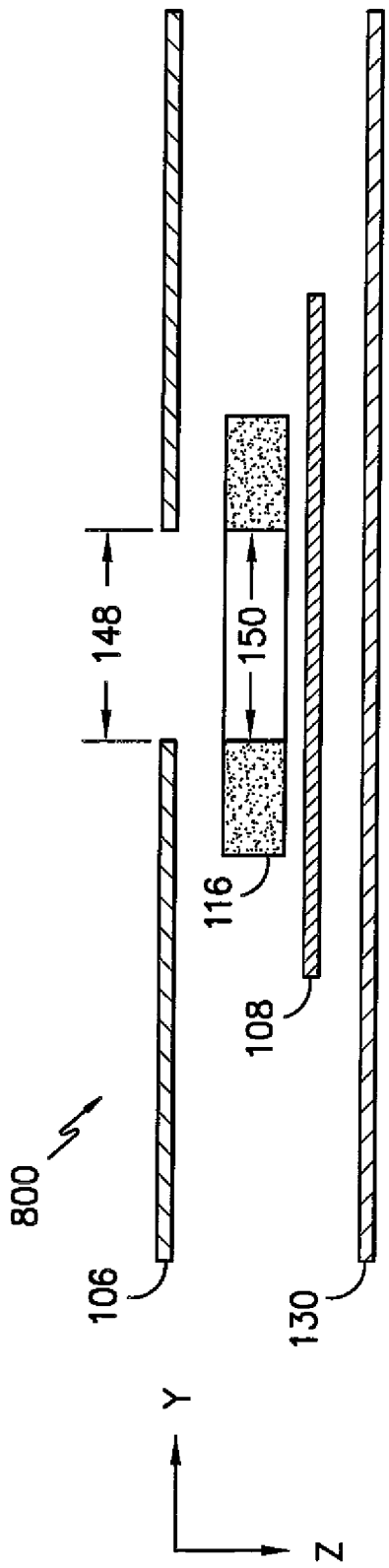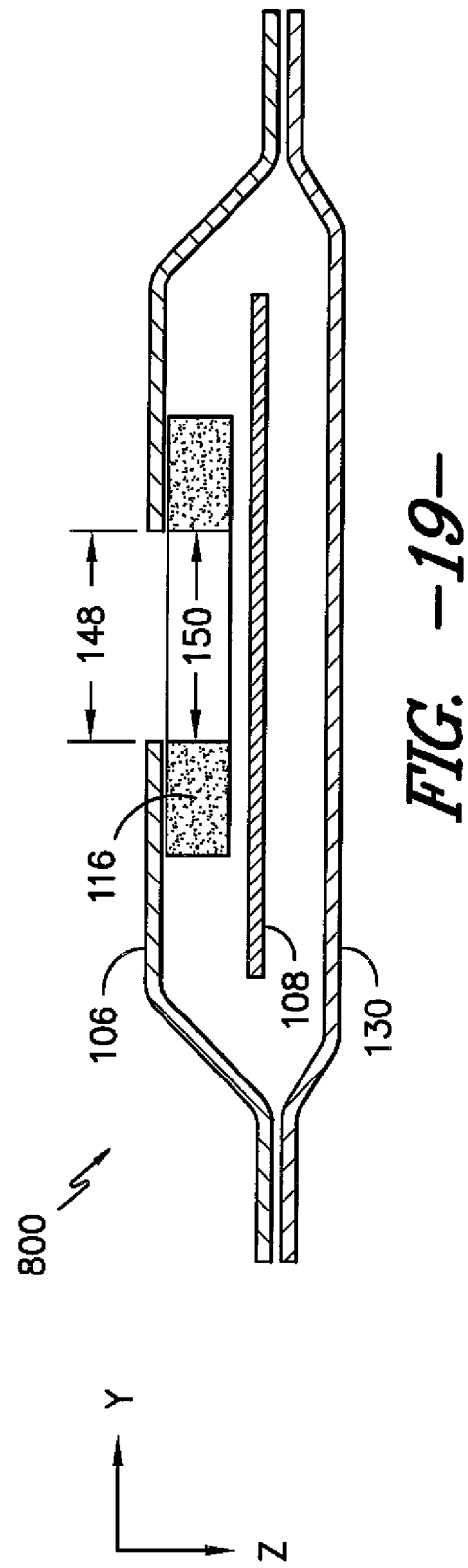

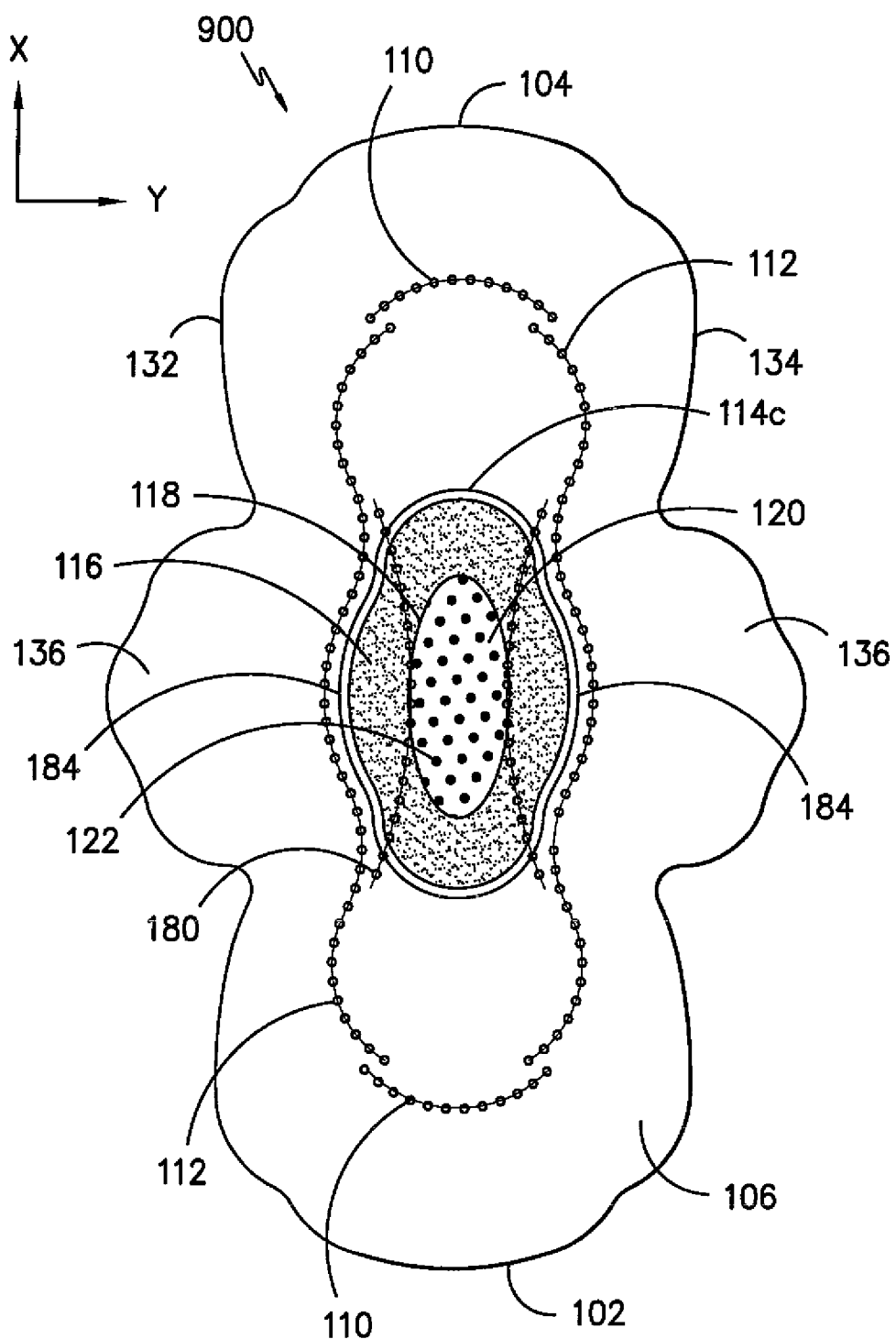
FIG. -20-

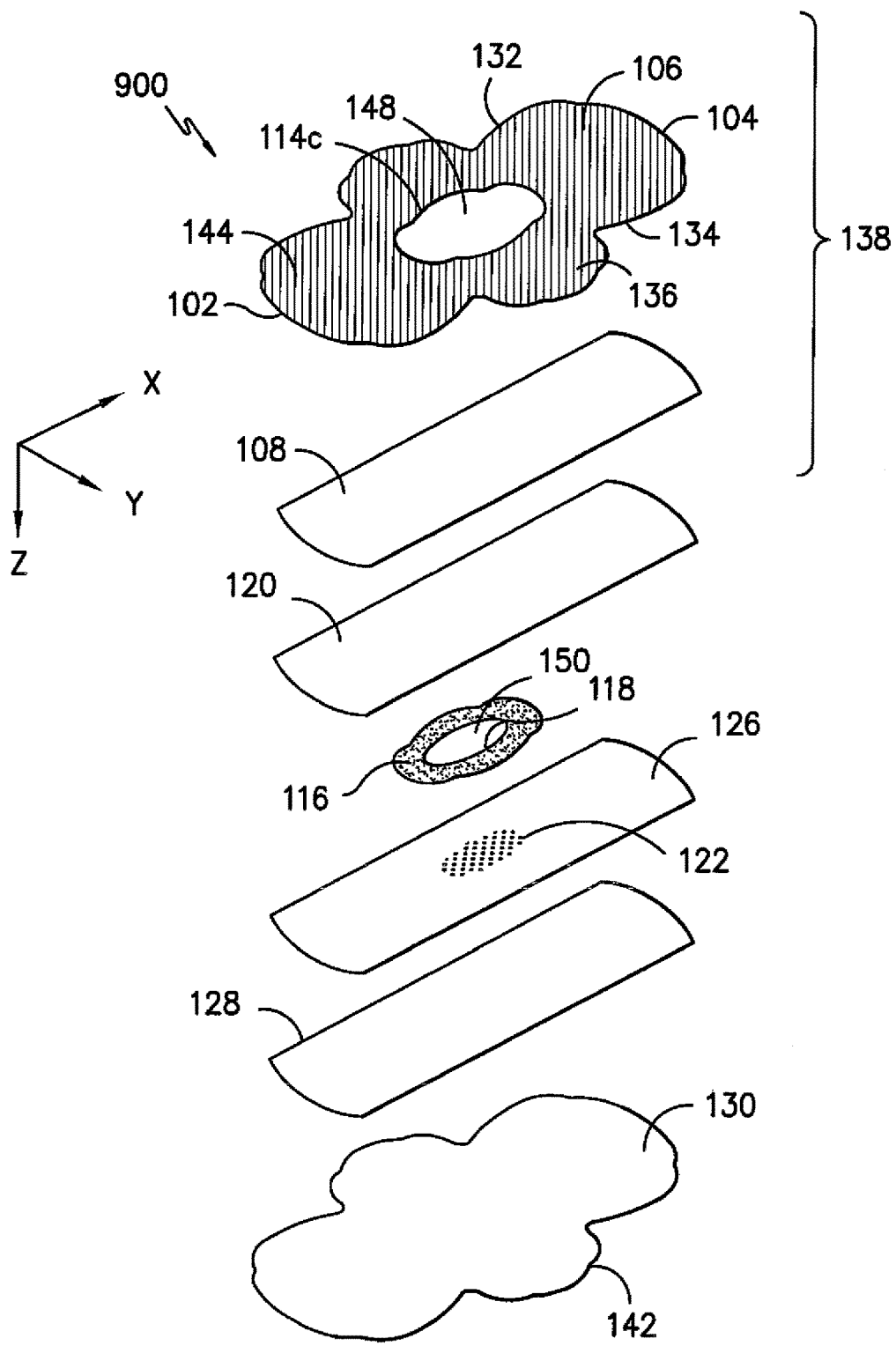
FIG. -21-

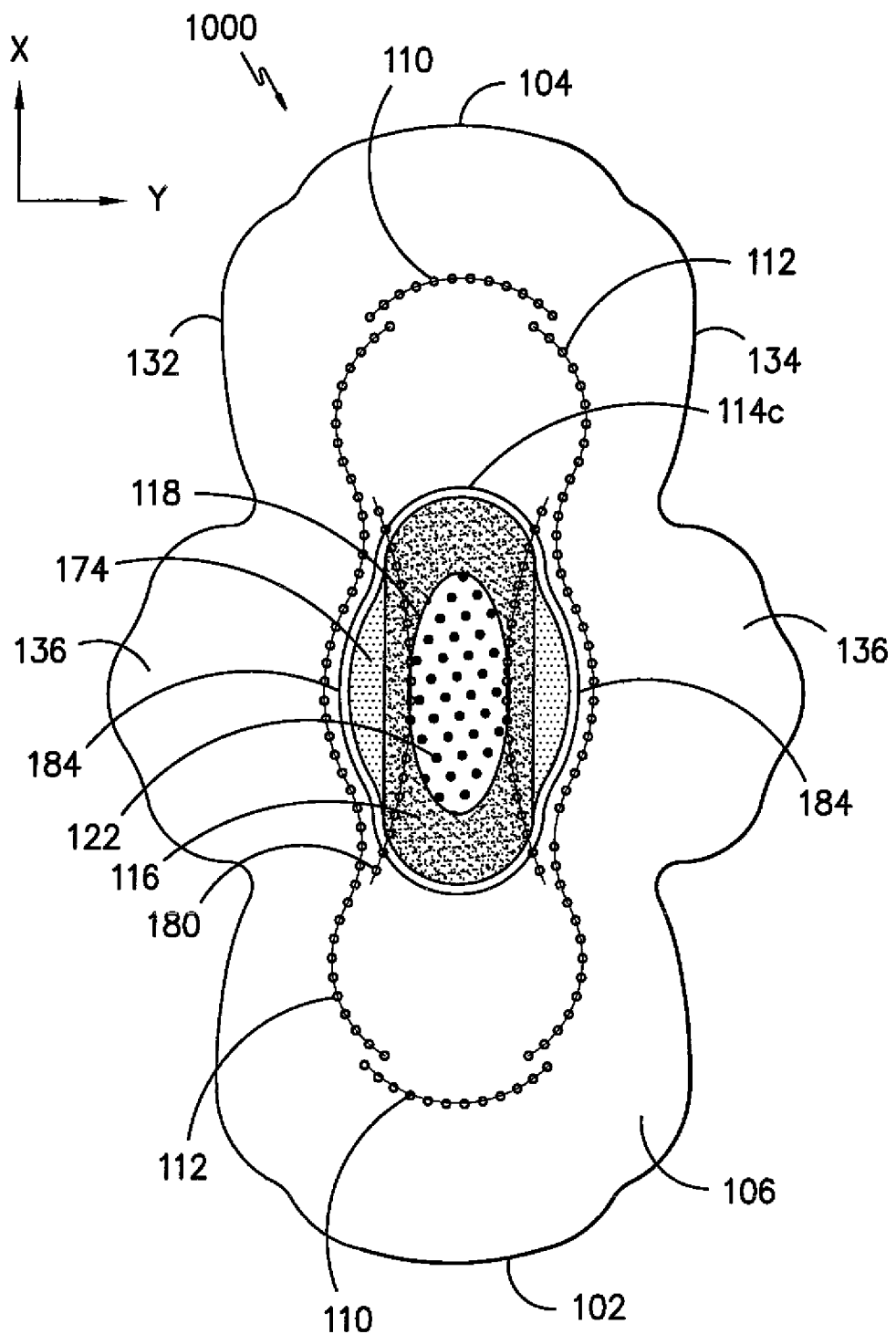
FIG. -22-

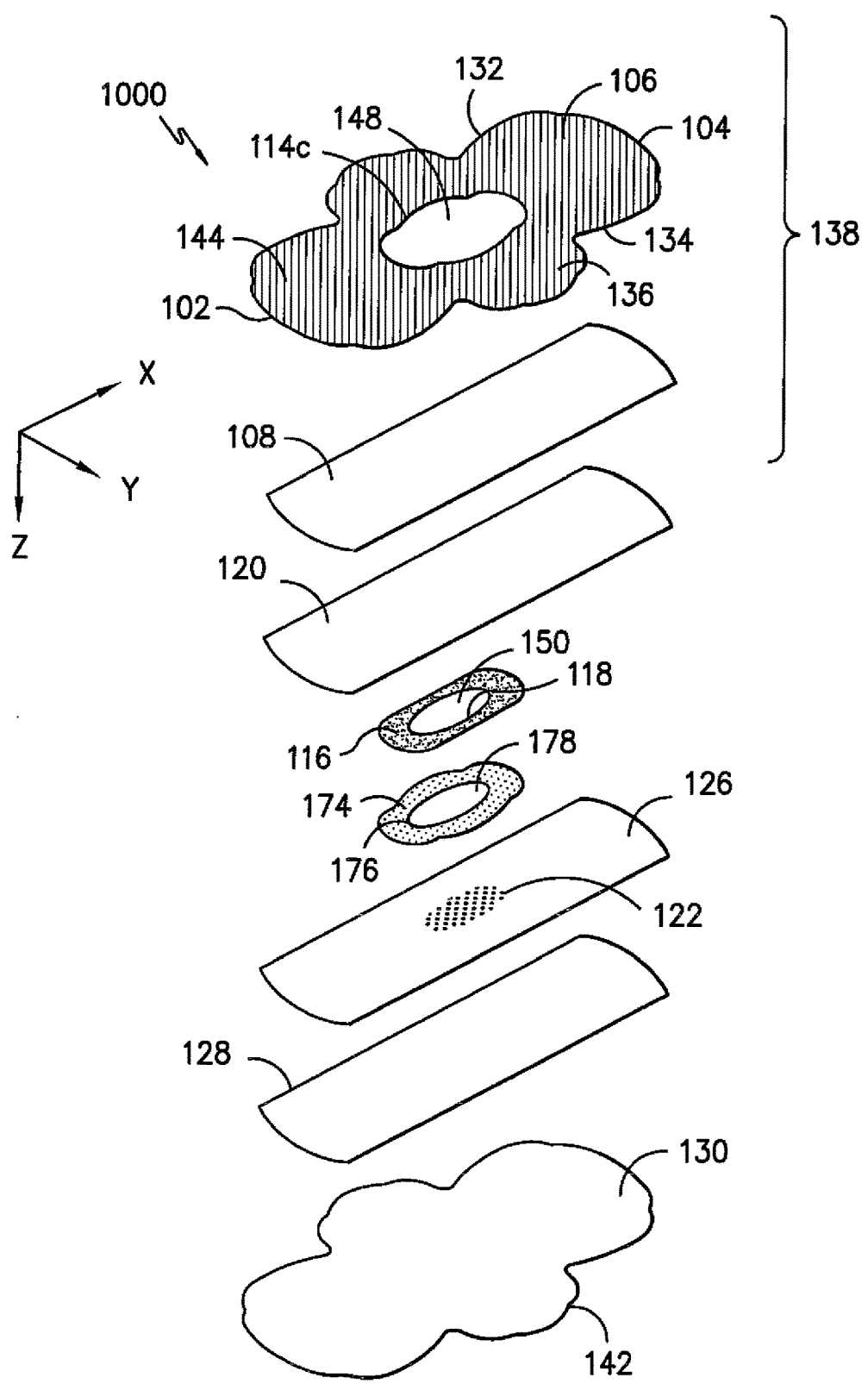
FIG. −23−

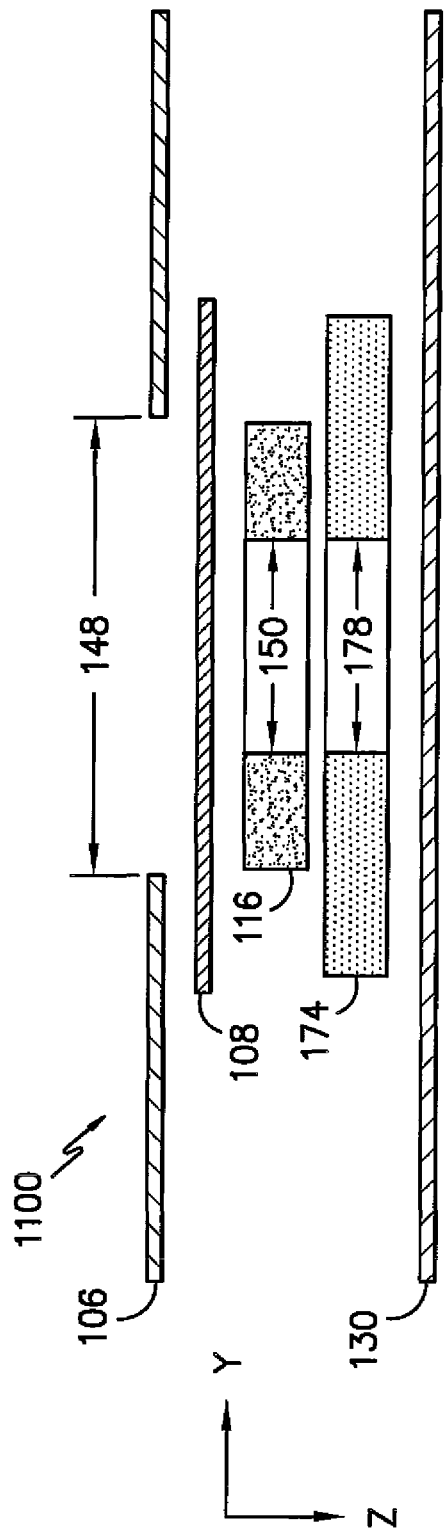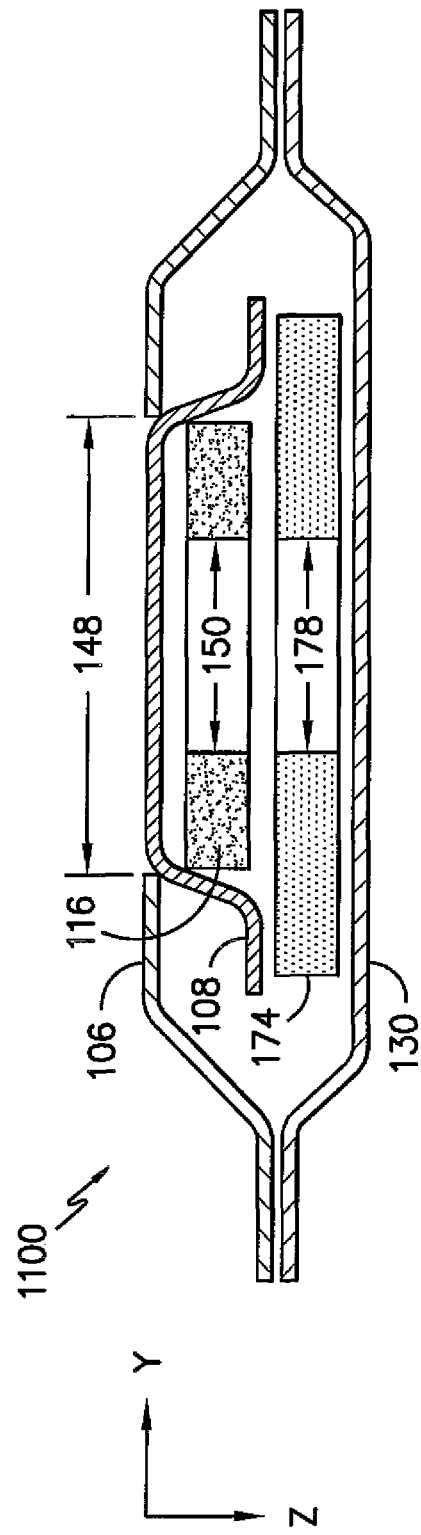

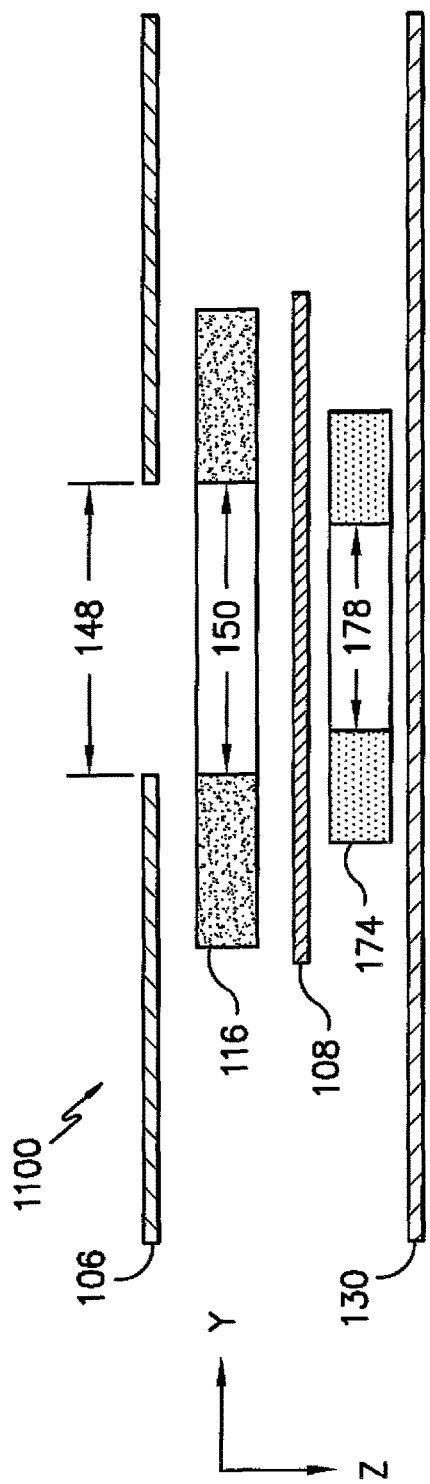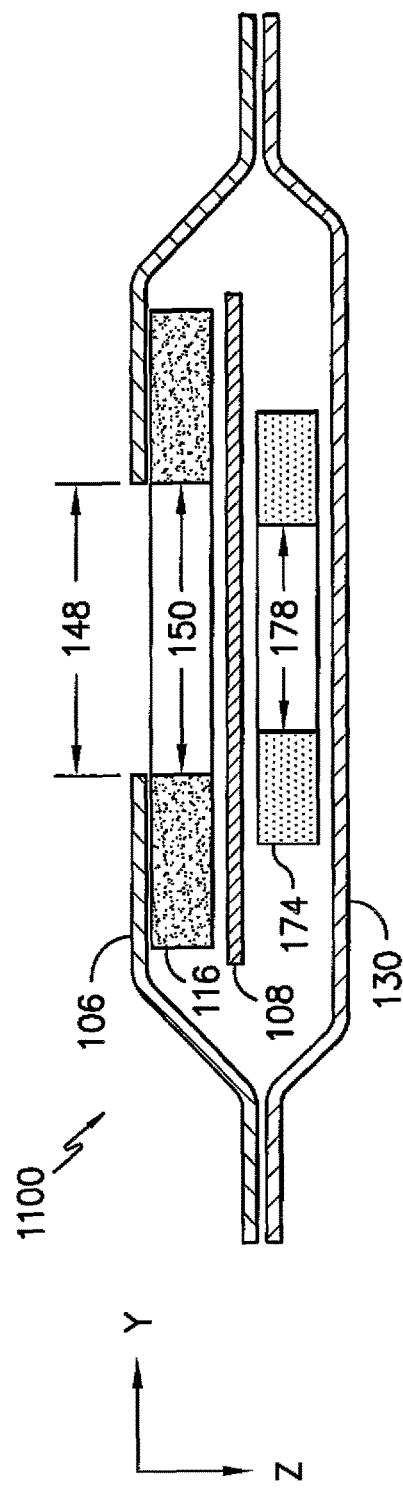

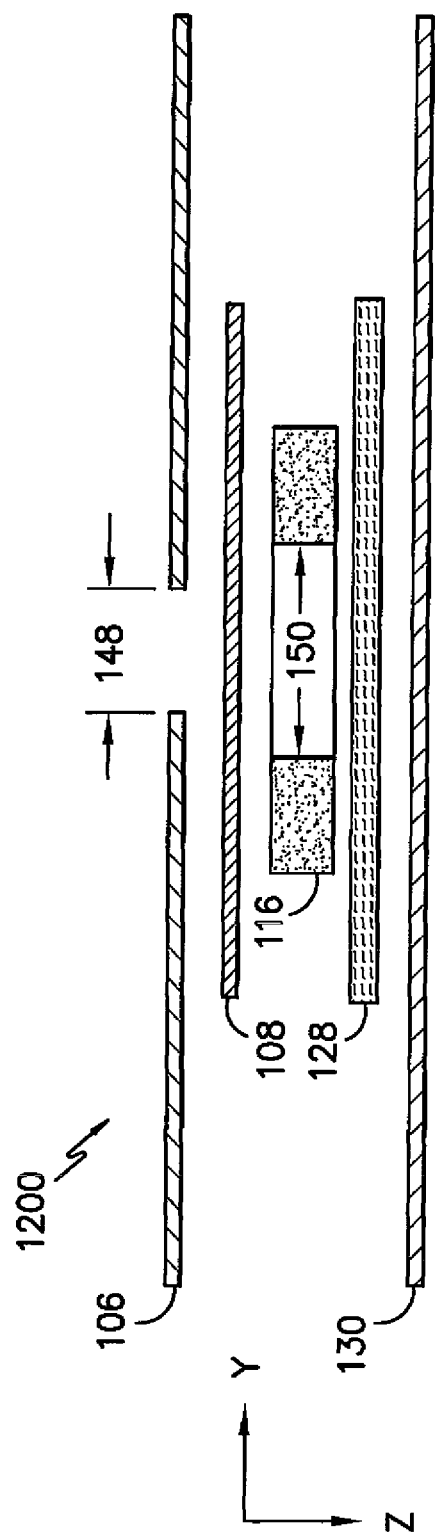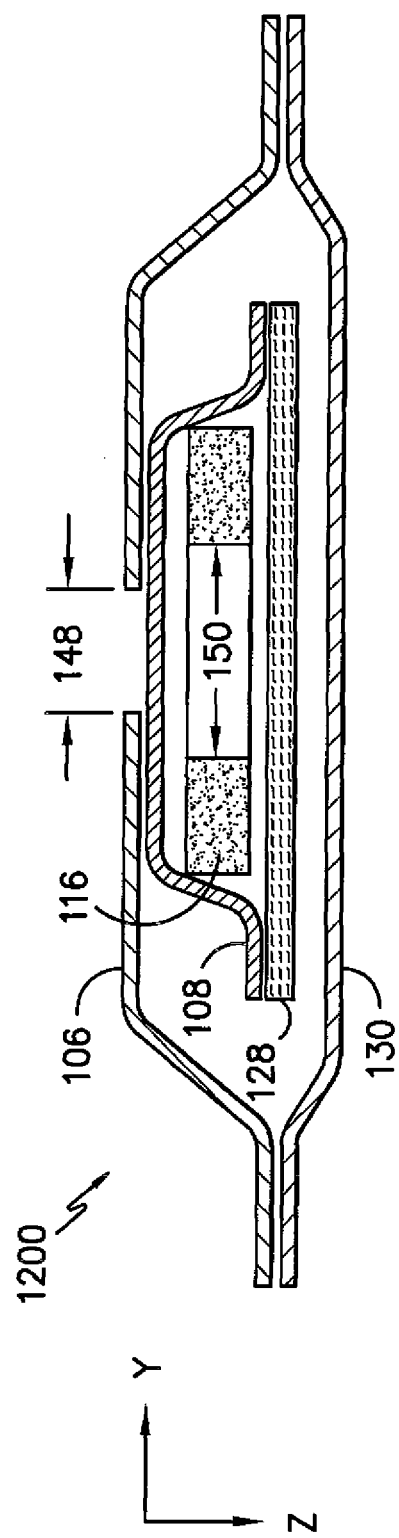

ABSORBENT ARTICLE WITH AN APERTURED MULTI-LAYERED TOPSHEET

CROSS REFERENCE TO RELATED APPLICATION

This application is the national stage entry of International Patent Application No. PCT/CN2012/085812 having a filing date of Dec. 4, 2012, the entire contents of which are incorporated herein by reference.

BACKGROUND OF THE INVENTION

Absorbent articles such as sanitary napkins, pantiliners, diapers, and incontinent pads are devices that are typically worn in the crotch region of an undergarment. Sanitary napkins and pantiliners are, for example, worn by women in a pair of panties that is normally positioned between the wearer's legs, adjacent to the perineum area. Sanitary napkins and pantiliners are designed to absorb and retain bodily fluids or discharges (e.g., menses) from the body of women and to prevent the wearer's body and clothing from soiling. Absorbent articles have been developed so that a liquid permeable topsheet can be positioned against the wearer's skin and can be configured to draw fluid away from the skin so that the wearer's skin remains relatively dry. The topsheet can contain multiple layers that work in conjunction with each other to be comfortable against the wearer's skin while also maintaining dryness against the skin of the wearer by providing for the rapid transfer of fluid away from the wearer's body. However, the ability of existing topsheets to remain smooth against the wearer's body is often inadequate. For instance, when the wearer moves around, the absorbent article is subjected to compressive forces between the wearer's legs. As a result, peaks and valleys can be formed in the topsheet and other layers, creating channels where fluid can pool, leading to the flow of fluid towards the edges of the absorbent article. This fluid can ultimately leak from the absorbent article, leading to soiling of the wearer's undergarments, clothing, or bedcoverings.

Meanwhile, the absorbent articles also include one or more additional layers below the topsheet that are designed to absorb and hold fluid that has entered the absorbent article. For instance, an absorbent core can be utilized to hold fluid that has passed through the liquid permeable topsheet layer to prevent the fluid from contacting the wearer's skin or from leaking outside the edges of the absorbent article. However, when the fluid enters the absorbent core, the absorbent core tends to be wetted at its upper surface. This, in turn, decreases the ability of additional fluid to flow downward and outward to the periphery of the absorbent core. As a result, additional fluid entering the absorbent article wicks sideways and leaks off of the edges of the pad instead of traveling downward into the absorbent core. Further, the fluid can pool on top of the absorbent article in situations where rapid gushes of fluid are applied to the absorbent article.

To help prevent such leakages and pooling from occurring, it is generally desirable to absorb and hold the fluids in a central region of the absorbent article. Attempts have been made to design absorbent articles, for instance, that have a thicker (i.e., three-dimensional) absorbent layer positioned in the center of the absorbent article that can trap fluid in a desired location of the absorbent article. However, such a layer is often bulky and can be uncomfortable to the wearer in that the bulkiness of the layer can prevent the absorbent article from conforming to the shape of the wearer's body. Although numerous types of three-dimensional structures have been employed in an attempt to improve the fit of absorbent articles against the body and to facilitate the capturing of excess fluid, many of these structures can be easily flattened by the compressive forces imparted during use. This results in an increased stain spread and the inability of the absorbent article to contain the fluid and corresponding stain in a central area of the structure.

In light of these problems, a need exists for an absorbent article that can draw and hold fluid in a centralized area of the absorbent article. A need also exists for an absorbent article that can prevent and mask the spread of stains resulting from a fluid insult. Further, a need exists for an absorbent article having a topsheet that can come into contact with the wearer's body and conform to the wearer's body while at the same time resisting compression in order to prevent leakage and provide an acceptable level of comfort.

SUMMARY OF THE INVENTION

In accordance with one embodiment of the present invention, an absorbent article is disclosed that generally extends in a plane defined by a longitudinal direction and a transverse direction. The article comprises a liquid permeable multi-layered topsheet, a first sub-topsheet layer situated beneath the topsheet, and a liquid impermeable baffle. The multi-layered topsheet defines a body-facing surface of the absorbent article, while the baffle defines a garment-facing surface of the absorbent article. The multi-layered topsheet extends in the longitudinal direction to define a distal end and an opposing proximal end of the absorbent article and in the transverse direction to define a first edge and an opposing second edge of the absorbent article. Further, the multi-layered topsheet has a length in the longitudinal direction, a width in the transverse direction, a longitudinal centerline, and a transverse centerline. In addition, the multi-layered topsheet comprises a first topsheet layer that is disposed above a second topsheet layer.

The first topsheet layer can comprise a nonwoven material, and the second topsheet layer can comprise an apertured film, although this is not required and both layers can be nonwoven materials, both layers can be films, or the first topsheet layer can be a film while the second topsheet layer can be a nonwoven material. The first topsheet layer defines a first opening having a first perimeter, and the first topsheet layer and the second topsheet layer are joined by a seal. The first sub-topsheet layer is positioned between the second topsheet layer and the baffle. The first sub-topsheet layer defines a second opening having a second perimeter, and the first perimeter substantially surrounds the second perimeter. However, in other embodiments, the second perimeter can substantially surround the first perimeter such that the second opening is larger (i.e., has a greater length in the longitudinal (x) direction and a greater width in the transverse (y) direction) than the first opening such that the entirety of the second opening is not contained within the first topsheet layer opening when viewed from the body-facing surface of the absorbent article in the z-direction.

In one embodiment, the first opening can have a substantially ovular shape, while in another embodiment, the first opening can have a complex shape, such as a generally oblong shape, wherein the perimeter is defined by one or more protrusions in the longitudinal direction and one or more protrusions in the transverse direction. In yet another embodiment, the multi-layered topsheet comprises an embossed region, wherein the embossed region substantially surrounds the first opening. The embossed region can have a shape that generally corresponds with the perimeter of the first opening.

Further, the first opening can be in substantial alignment with the longitudinal centerline. In addition, the first opening can be in substantial alignment with the transverse centerline or it can be located towards the distal end or proximal end of the first topsheet layer. Regardless of its location, the first opening can have a length that is from about 15% to about 80% of the length of the first topsheet layer and a width that is from about 20% to about 80% of the width of the first topsheet layer.

Turning now to the seal between the first topsheet layer and the second topsheet layer, in one embodiment, the seal is generally continuous. The seal can be formed by an adhesive bond, a pressure bond, a thermal bond, an ultrasonic bond, or a combination thereof. Further, at least a portion of the seal can be generally coextensive with an embossed region if present. Generally, the first topsheet layer can be disposed above the second topsheet layer at the distal end, the proximal end, the first edge, and the second edge of the absorbent article, and at least one printed graphic can be visible from the body-facing surface of the absorbent article along each of the distal end, proximal end, first edge, and second edge.

In one embodiment, the length of the second topsheet layer ranges from about 30% to about 100% of the length of the first topsheet layer. Meanwhile, the width of the second topsheet layer can range from about 10% to about 100% of the width of the first topsheet layer.

In still another embodiment, a first liquid permeable layer can be positioned between the second topsheet layer and the first sub-topsheet layer. Further, a second liquid permeable layer can be positioned between the first sub-topsheet layer and the baffle, wherein a pattern is printed on the second liquid permeable layer such that the pattern is visible from the body-facing surface of the absorbent article. The first and second liquid permeable layers can be surge layers, transfer layers, distribution layers, or combinations thereof. Additionally, when numerous layers are utilized, each layer can have a distinct color, shading, or pattern to further aid the wearer in placing the absorbent article in the proper location.

In yet another embodiment, a portion of the second topsheet layer can be exposed beneath the first opening such that the exposed portion of the second topsheet layer forms part of the body-facing surface of the absorbent article, and the seal between the two layers can generally correspond with the first perimeter. Further, the seal can be generally concentric with the first perimeter.

In another embodiment, the second topsheet layer can define a third opening having a third perimeter, and the first perimeter can substantially surround the third perimeter such that the seal between the first topsheet layer and the second topsheet layer can generally correspond with the first perimeter. On the other hand, the third perimeter can instead substantially surround the first perimeter so that the seal generally can correspond with the third perimeter. Further, when both the first topsheet layer and the second topsheet layer include an opening, the absorbent article further comprises a third topsheet layer that is disposed between the second topsheet layer and the first sub-topsheet layer.

In still another embodiment, an absorbent core can be disposed between the multi-layered topsheet and the baffle. Further, the absorbent core can be disposed between the first sub-topsheet layer and the baffle.

In yet another embodiment, the absorbent article further comprises a second sub-topsheet layer positioned between the first sub-topsheet layer and the baffle. The second sub-topsheet layer can define a fourth opening having a fourth perimeter. Additionally, the second sub-topsheet layer can have a shape that includes a first bulge facing the first edge in the transverse direction and a second bulge facing the second edge in the transverse direction, wherein the bulges are visible from the body-facing surface of the absorbent article.

In an additional embodiment, the absorbent article comprises a third sub-topsheet layer positioned at the distal end of the absorbent article between the second topsheet layer and the baffle. In this embodiment, the first topsheet layer defines a fifth opening having a fifth perimeter, wherein the third sub-topsheet layer exists in the same plane as the first sub-topsheet layer. Further, the third sub-topsheet layer has a substantially ovular shape.

In another embodiment, the present disclosure is directed to an absorbent article that generally extends in a plane defined by a longitudinal direction and a transverse direction. The absorbent article comprises, in sequential order from a body-facing surface to a garment facing surface of the absorbent article, the following: a liquid permeable multi-layered topsheet, a first liquid permeable surge layer, a sub-topsheet layer, a second liquid permeable surge layer, an absorbent core, and a baffle. The liquid permeable multi-layered topsheet comprises a first topsheet layer disposed above a second topsheet layer, wherein the first topsheet layer defines a first opening having a first perimeter, wherein the first topsheet layer and the second topsheet layer are joined by a seal, and further wherein the multi-layered topsheet extends in the longitudinal direction to define a distal end and an opposing proximal end of the absorbent article and in the transverse direction to define a first edge and an opposing second edge of the absorbent article. Meanwhile, the sub-topsheet layer defines a second opening having a second perimeter, wherein the first perimeter substantially surrounds the second perimeter. Further, a pattern is printed on the second liquid permeable surge layer such that the pattern is present on the first topsheet layer and visible from the body-facing surface of the absorbent article. In addition, at least one printed graphic is visible from the body-facing surface of the absorbent article along each of the distal end, proximal end, first edge, and second edge of the absorbent article.

Other features and aspects of the present invention are discussed in greater detail below.

BRIEF DESCRIPTION OF THE FIGURES

A full and enabling disclosure of the present invention, including the best mode thereof, directed to one of ordinary skill in the art, is set forth more particularly in the remainder of the specification, which makes reference to the appended figures in which:

FIG. 11 is a top view of another embodiment of the absorbent article of the present invention;

FIG. 12 is an exploded view of still another embodiment of the absorbent article of the present invention;

FIG. 13 is an exploded view of yet another embodiment of the absorbent article of the present invention;

FIG. 14 is an exploded cross-sectional view of one embodiment of the absorbent article of the present invention taken at the transverse centerline;

FIG. 15 is a cross-sectional view of the embodiment of the absorbent article of FIG. 14 once assembled;

FIG. 16 is an exploded cross-sectional view of another embodiment of the absorbent article of the present invention taken at the transverse centerline;

FIG. 17 is a cross-sectional view of the embodiment of the absorbent article of FIG. 16 once assembled;

FIG. 18 is an exploded cross-sectional view of yet another embodiment of the absorbent article of the present invention taken at the transverse centerline;

FIG. 19 is a cross-sectional view of the embodiment of the absorbent article of FIG. 18 once assembled;

FIG. 20 is a top view of another embodiment of the absorbent article of the present invention;

FIG. 21 is an exploded perspective view of FIG. 20;

FIG. 22 is a top view of another embodiment of the absorbent article of the present invention;

FIG. 23 is an exploded perspective view of FIG. 22;

FIG. 24 is an exploded cross-sectional view of yet another embodiment of the absorbent article of the present invention taken at the transverse centerline;

FIG. 25 is a cross-sectional view of the embodiment of the absorbent article of FIG. 24 once assembled;

FIG. 26 is an exploded cross-sectional view of yet another embodiment of the absorbent article of the present invention taken at the transverse centerline;

FIG. 27 is a cross-sectional view of the embodiment of the absorbent article of FIG. 26 once assembled;

FIG. 28 is an exploded cross-sectional view of still another embodiment of the absorbent article of the present invention taken at the transverse centerline; and FIG. 29 is a cross-sectional view of the embodiment of the absorbent article of FIG. 28 once assembled.

Figure 1:
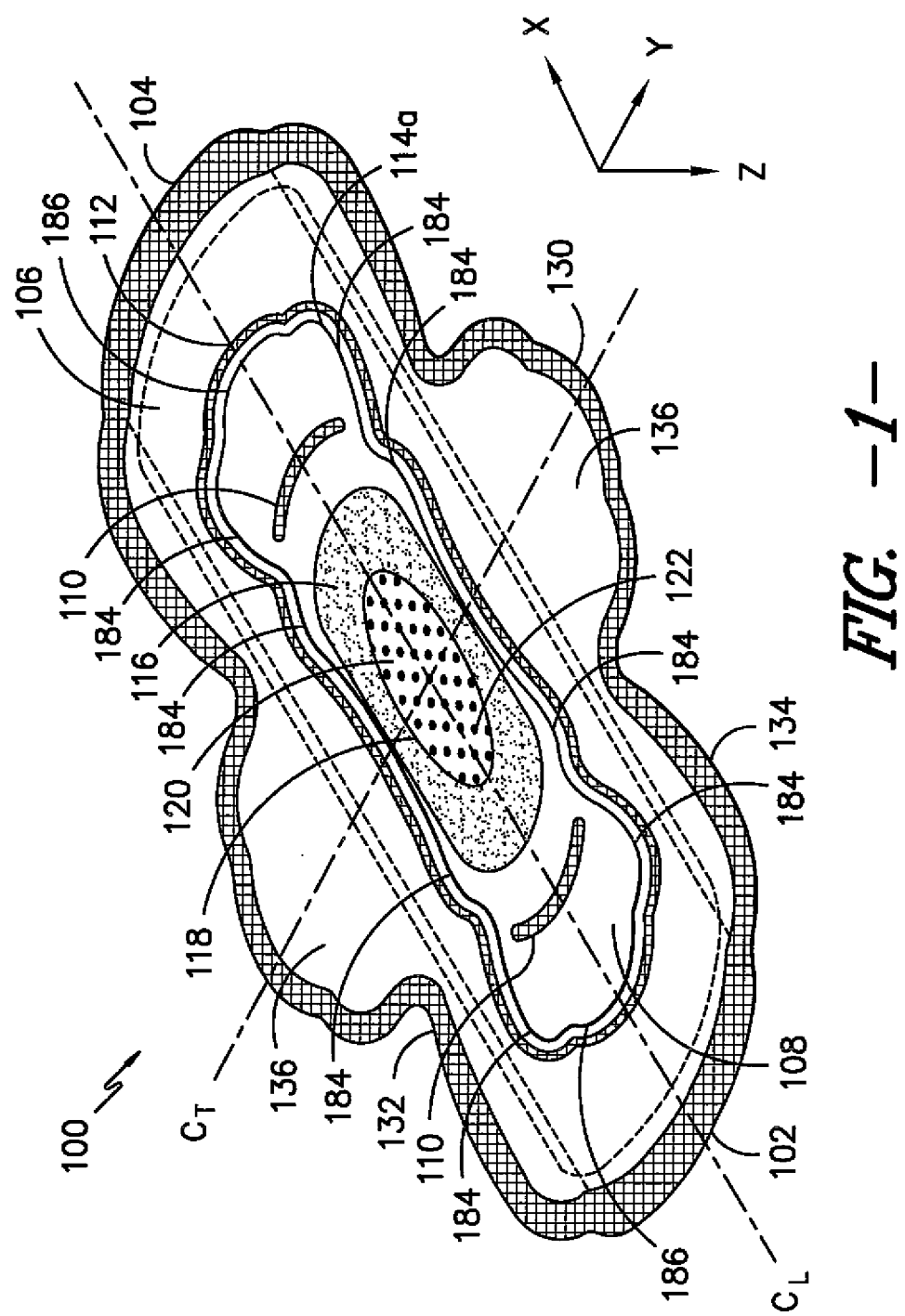
FIG. 1 is a perspective view of one embodiment of the absorbent article of the present invention.

Repeat use of reference characters in the present specification and drawings is intended to represent the same or analogous features or elements of the invention.

DETAILED DESCRIPTION OF REPRESENTATIVE EMBODIMENTS

Definitions

As used herein, the term "body-facing surface" generally refers to an outwardly facing surface of an absorbent article that is intended to be disposed toward or placed adjacent to the body of a wearer during ordinary use. This surface may be defined by a multi-layered topsheet having one or more layers, which also includes an opposing inwardly facing surface.

As used herein, the term "garment-facing surface" generally refers to an outwardly facing surface of an absorbent article that is intended to be disposed away from the body of a wearer during ordinary use. The surface is typically placed adjacent to the wearer's undergarments when the article is worn. This surface may be defined by a baffle, which also includes an opposing inwardly facing surface.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a feminine care absorbent article such as a sanitary napkin or pad that can conform to the wearer's body, can be comfortable against the wearer's skin, and can provide the wearer with a visual cue as to the proper placement of the absorbent article, while at the same time functioning to maintain a high level of dryness and inhibit the leakage of bodily fluids at the peripheral edges of the absorbent article.

The absorbent article, which includes a liquid permeable multi-layered topsheet, at least a first sub-topsheet layer, and a liquid impermeable baffle, generally extends in a plane defined by a longitudinal direction to define a longitudinal centerline, a distal end, and an opposing proximal end and a transverse direction to define a transverse centerline, a first edge, and an opposing second edge. The multi-layered topsheet, which defines a body-facing surface of the absorbent article, is dual-zoned and includes at least a first topsheet layer that is disposed above a second topsheet layer. It is to be understood that so that the two layers can be in direct contact with each other in some embodiments, while in other embodiments, one or more other absorbent article layers can be disposed between the first topsheet layer and the second topsheet layer. The first topsheet layer includes an opening defined by a perimeter that can leave a portion of the second topsheet layer exposed. However, it is also to be understood that the second topsheet layer can also include an opening defined by a perimeter, where the opening is situated beneath the first topsheet layer opening. The second topsheet layer opening can be smaller than the first topsheet layer opening such that when the second topsheet layer opening is situated below the first topsheet layer opening, a portion of the second topsheet layer remains exposed at the body-facing surface of the absorbent article so that the second topsheet layer can contact the wearer's skin and form part of the body-facing surface of the absorbent article. On the other hand, in another embodiment, the second topsheet layer opening can be larger than the first topsheet layer opening such that when the second topsheet layer opening is situated below the first topsheet layer opening, the second topsheet layer is not exposed. Instead, a third topsheet layer can be present that is exposed at the body-facing surface of the absorbent article so that the third topsheet layer can be in contact the wearer's skin and form part of the body-facing surface of the absorbent article. In addition, the aforementioned first and second topsheet layer openings can have simple shapes or more complex shapes. For instance, an opening can have a complex oblong shape where the perimeter of the opening is defined by one or more protrusions in the longitudinal (x) direction and/or transverse (y) direction. Generally, the first and second topsheet layer openings function to draw bodily fluids away from the skin of the wearer and towards the lower layers of the absorbent article that are positioned below the multi-layered topsheet in the z-direction via a funnel-like effect. Moreover, the openings can permit the multi-layered topsheet to conform to the wearer's body by creating a means by which the multi-layered topsheet can bend. Further, the openings can also provide a visual cue as to the proper placement of the absorbent article.

It is to be understood that the first topsheet layer and the second topsheet layer can be made of any suitable topsheet layer material or combination of materials. Suitable materials include liquid permeable non-woven materials, woven materials, films, etc. It is also to be understood that the first topsheet layer and the second topsheet layer can be made of the same material or any combination of suitable topsheet layer materials. If one of the topsheet layers includes a film, the film can be apertured to impart liquid permeability to the film. The apertures in the film can function to draw bodily fluids away from the skin of the wearer to maintain a dry topsheet against the skin of the wearer. Further, regardless of the material or combination of materials used for the first topsheet layer or the second topsheet layer, the material or combination of materials can be comfortable and soft against the skin of the wearer.

Additionally, when the first topsheet layer opening is larger than the optional second topsheet layer opening or when there is no second topsheet layer opening, the first topsheet layer and the second topsheet layer can be joined together by a seal that generally corresponds with the portions of the perimeter of the first topsheet layer opening that overlap with the second topsheet layer. However, if the second topsheet layer has an opening situated below the first topsheet layer opening such that the second topsheet opening is larger than the first topsheet layer opening, then the first topsheet layer and the second topsheet layer can be joined together by a seal that generally corresponds with the portions of the perimeter of the second topsheet layer opening that overlap with the first topsheet layer. Further, the first topsheet layer and the second topsheet layer are sealed in such a manner that the area at which the two layers are sealed generally has the appearance and feel of a single, continuous layer instead of two separate layers that have been sealed together.

In addition to having a first topsheet layer and a second topsheet layer, the multi-layered topsheet can include at least one embossed region. The embossed region can be located about the absorbent article such that at least a portion of the seal between the first topsheet layer and the second topsheet layer is generally coextensive with the embossed region. It is also to be understood that in some instances, it may be possible for the embossed region to form the seal between the first and second topsheet layers, although generally the seal and any embossed regions are separate. The embossed region can provide an aesthetically pleasing appearance to the multi-layered topsheet and also creates a channel to direct fluid flow away from the periphery of the topsheet to prevent pooling of fluids at contact points along the multi-layered topsheet.

Meanwhile, the absorbent article also includes a baffle that defines a garment-facing surface of the absorbent article and a first sub-topsheet layer that is positioned between the multi-layered topsheet and the baffle. It is to be understood, however, that other layers can be disposed between the multi-layered topsheet and the first sub-topsheet layer, and between the first sub-topsheet layer and the baffle, such as additional topsheet layers, fluid intake layers, surge layers, transfer layers, distribution layers, and absorbent core layers, all of which may or may not have additional openings to further enhance the absorbent article's ability to funnel fluid into a desired location in the absorbent article. Further, in some instances, the first sub-topsheet layer may actually be located between the first topsheet layer and the second topsheet layer so that the second topsheet layer is positioned below the first sub-topsheet layer in the z-direction. In this case, the first topsheet layer and the second topsheet layer can sandwich the first sub-topsheet layer.

Generally, the first sub-topsheet layer defines a first sub-topsheet layer opening that is situated below one or more of the multi-layered topsheet layer openings in the z-direction away from the body-facing surface of the absorbent article. Regardless of the structure of the first sub-topsheet layer, the first sub-topsheet layer opening is utilized in conjunction with the first topsheet layer opening and/or the optional second topsheet layer opening to create a funnel-like configuration to further draw fluid towards a desired location in the absorbent article, such as a central region of the first sub-topsheet layer or absorbent core. For instance, the first sub-topsheet layer and its defined opening can create a well-like structure or cup for holding fluid. The absorbent article can also include additional layers disposed between the second topsheet layer of the multi-layered topsheet and the baffle, such as additional multi-layered topsheet layers, additional absorbent core layers, fluid intake layers, distribution layers, transfer layers, surge layers, etc.

Referring now to FIGS. 1-27, various embodiments of a feminine care absorbent article of the present invention will now be described. As generally shown, the feminine care absorbent articles 100-1200 of FIGS. 1-4 and 11-27 include a multi-layered topsheet 138 that generally overlies a baffle 130. The multi-layered topsheet 138 has a first topsheet layer 106 disposed above a second topsheet layer 108. Further, the absorbent articles include a first sub-topsheet layer 116 having an opening 150 such that the opening 150 lies within and is generally surrounded or framed by the area created by any openings in either layer 106 or 108 of the multi-layered topsheet. The first sub-topsheet layer 116 can be an additional topsheet layer, a surge layer, a fluid intake layer, an absorbent core layer, a fluid distribution layer, or any other layer suitable for use in an absorbent article. It is to be understood that the absorbent article may optionally include other layers in addition to the multi-layered topsheet 138, the first sub-topsheet layer 116, and the baffle 130, such as, for example, surge layers 120 and 126, a distal end sub-topsheet layer 168, additional topsheet layers, absorbent core layers such as absorbent core 128, fluid intake layers, distribution layers, transfer layers, additional sub-topsheet layers, etc. The components and features of the absorbent article of FIGS. 1-27 are discussed in more detail below.

First, the multi-layered topsheet 138 provides comfort to the wearer in that it is designed to conform to the wearer's body and also has an aesthetically pleasing appearance, while at the same time serving to direct bodily exudates away from the body-facing surface 144 of the absorbent article and toward lower layers of the absorbent article, such as a sub-topsheet layer or absorbent core, which are positioned below the multi-layered topsheet 138 in the z-direction. The multi-layered topsheet 138 is liquid permeable and generally extends over the upper, bodyside surface of the baffle 130 at the peripheral edges of the absorbent article. The multi-layered topsheet 138 defines a distal end 102 and an opposing proximal end 104 in the longitudinal (x) direction, as well as a first edge 132 and an opposing second edge 134 in the transverse (y) direction of the absorbent article. The multi-layered topsheet 138 also defines a longitudinal centerline $C_L$ and a transverse center line $C_T$. Although the proximal and distal ends are shown herein as the front and rear ends of the article, respectively, the terms "proximal" and "distal" do not necessarily refer to the rear and front ends of the topsheet as such terms are employed only for the sake of convenience. In any event, the shape of the proximal and/or distal ends and/or edges of the topsheet may be configured to help improve the comfort of the article during use.

Generally, the multi-layered topsheet 138 is constructed of liquid permeable materials known in the art that are easily penetrated by bodily exudates. As described above, the multi-layered topsheet 138 can include at least two layers, and each of the layers themselves can comprise multiple layers of materials. Regardless of the number of layers utilized, the multi-layered topsheet 138 typically has a basis weight of less than about 100 grams per square meter (gsm), and in some embodiments, from about 10 gsm to about 60 gsm. In the particular embodiments described in the present disclosure, the multi-layered topsheet 138 defines a body-facing surface 144 of the absorbent article and includes at least (1) a first topsheet layer 106 defining at least one opening 148, and (2) a second topsheet layer 108 that may or may not be exposed at the opening in the first topsheet layer 106 depending on whether or not the second topsheet layer 108 has an opening situated below the first topsheet layer opening 148. As shown in FIGS. 3, 6, 12, and 13, the first topsheet layer 106 is disposed directly above the second topsheet layer 108 in the z-direction, where additional layers are present under the second topsheet layer 108 and towards an absorbent layer in the z-direction. However, it is to be understood that the multi-layered topsheet 138 can include other additional layers that may or may not have openings and that may be located between the first topsheet layer 106 and the second topsheet layer 108, as shown in FIGS. 18-19 and 26-27. The first topsheet layer 106, second topsheet layer 108, and any additional layers can be manufactured from a combination of a wide variety of materials such as, for example, woven materials, nonwoven webs, apertured nonwoven webs, porous foams, reticulated foams, apertured plastic films, and laminates thereof.

For instance, the first topsheet layer 106, the second topsheet layer 108, and/or any additional layers in the multi-layered topsheet can include a nonwoven material. The nonwoven material can be a meltblown web, a spunbond web, a hydroentangled web, a bonded card web, a thermally bonded carded web, a spunbond web of bicomponent fibers, or a bonded carded web of bicomponent fibers. Further, the first topsheet layer can be formed from nylon, polyester, polyolefins such as polypropylene or polyethylene, copolymers of polypropylene and polyethylene, linear low-density polyethylene, aliphatic esters such as polylactic acid, other heat-bondable fibers, or combinations thereof. A specific example of a suitable material for the first topsheet layer 106, the second topsheet layer 108, or any additional layers in the multi-layered topsheet is a bonded carded web made of polypropylene and polyethylene such as that used as topsheet stock for KOTEX® pantiliners and obtainable from Sandler AG (Germany). It should be understood that either one or both of the at least two topsheet layers 106 and 108 can be formed from a nonwoven material. Further, if both the first topsheet layer 106 and the second topsheet layer 108 are made from a nonwoven material, the second topsheet layer 108 can have added three-dimensional characteristics, apertures, or other features to improve the level of dryness imparted to the absorbent article at the area of the second topsheet layer 108 as compared to the first topsheet layer 106.

In another embodiment, the first topsheet layer 106, the second topsheet layer 108, or any additional layers in the multi-layered topsheet can include a film. The film can be made of any suitable polymer. Suitable polymers that can be used to form any layer of the multi-layered topsheet 138 include any material which can be formed into a film including, but not limited to, polyolefins and polyacrylates, as well as copolymers and blends thereof. For instance, polymers from which to form any layer of the multi-layered topsheet include, but are not limited to, polyethylene, low density polyethylene, linear low density polyethylene, polypropylene, polyvinyl chloride, polyvinyl alcohol, ethylene vinyl acetate, starch base resins, cellulose esters, polyurethanes, polycaprolactone, or combinations thereof. A specific example of a suitable material for any of the layers in the multi-layered topsheet is a three-dimensional, apertured film made of polyethylene. For instance, the film can be a perforated film having apertures that are tapered capillaries. Further, the film can have a run off percent of less than about 10 percent and an increased liquid flow rate through the tapered capillaries. The method of making such a film can include a surface treatment, although such a treatment is not required.

Figure 10:
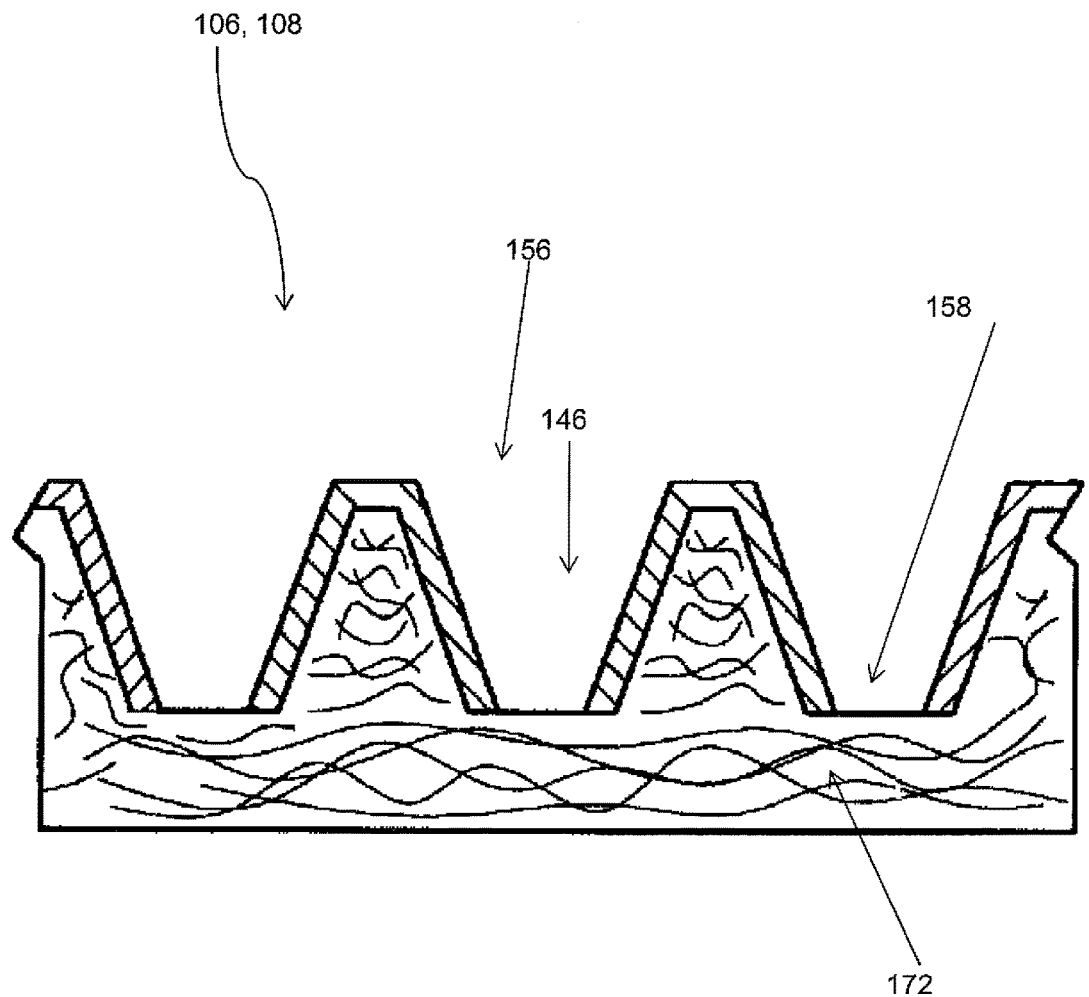
FIG. 10 is a side view of one embodiment of a three-dimensional, apertured film that may be used in the absorbent article of the present invention.

Referring now to FIG. 10, a film that can be used as the first topsheet layer 106, the second topsheet layer 108, or any other layer of the absorbent article is shown. The first topsheet layer 106 or the second topsheet layer 108 can be a three-dimensional film structure having a plurality of apertures 146, each of which can be tapered to have a base 156 (i.e., the widest point of the opening), and an apex 158 (i.e., the narrowest point of the opening). The apexes 158 of the apertures 146 may be in contact with any other suitable lower layer 172 of the absorbent article. Meanwhile, the bases 156 of the apertures 152, which are wider than the apexes 158, can be in contact with an upper layer, if any, of the absorbent article. For instance, when the film is used as the first topsheet layer 106, the apexes 158 can be in contact with the second topsheet layer 108 or any layer between the first topsheet layer 106 and the second topsheet layer 108 in the z-direction, while the bases 156 can be located at the body-facing surface 144 of the absorbent article. Meanwhile, if the film is used as the second topsheet layer 108, the apexes 158 can be in contact with the first sub-topsheet layer 116 or any other layer below the second topsheet layer 108 in the z-direction, such as an additional topsheet layer, a surge layer, an absorbent core layer, an intake layer, a distribution layer, etc., while the bases 156 can be in contact with the first topsheet layer 106 or any layer between the second topsheet layer 108 and the first topsheet layer 106 in the z-direction.

In one embodiment, the first topsheet layer 106 and/or the second topsheet layer 108 can include a film made of a thermoplastic material that is provided with a multiplicity of apertures 146 that resemble tapered capillaries. The first topsheet layer 106 and/or the second topsheet layer 108 can also include other types of apertured plastic films that are not thermoplastic. The type of film used depends on the type of processing that first topsheet layer 106 and second topsheet layer 108 are subjected to during the manufacture of the multi-layered topsheet 138. For instance, thermoplastic films can be used as the first topsheet layer 106 and the second topsheet layer 108 when the first topsheet layer 106 and the second topsheet layer 108 are integrally formed into a composite structure by melting. Other types of apertured films include, but are not limited to hydro-formed films.

Figure 3:
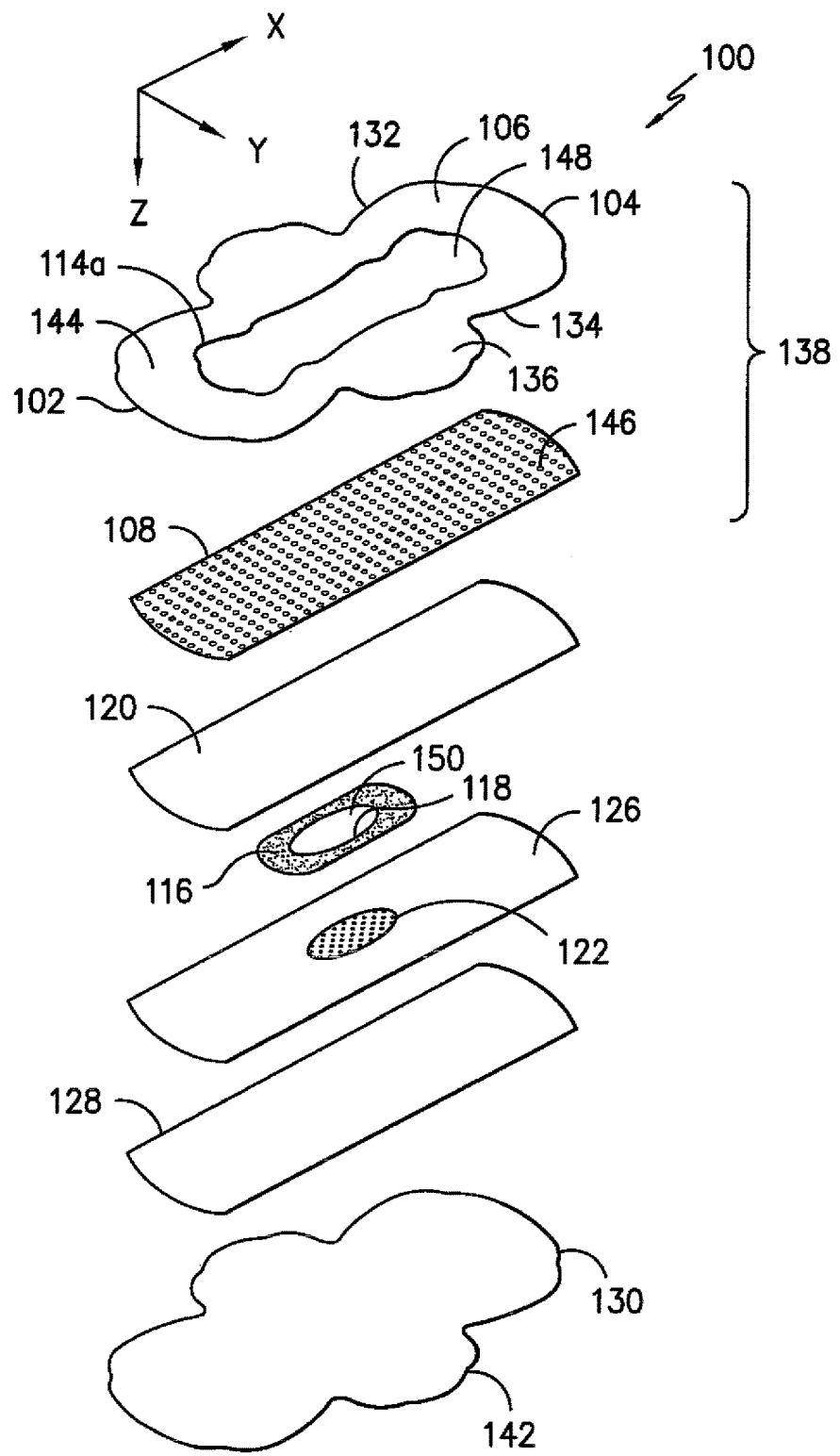
FIG. 3 is an exploded perspective view of FIG. 1.
Figure 6:
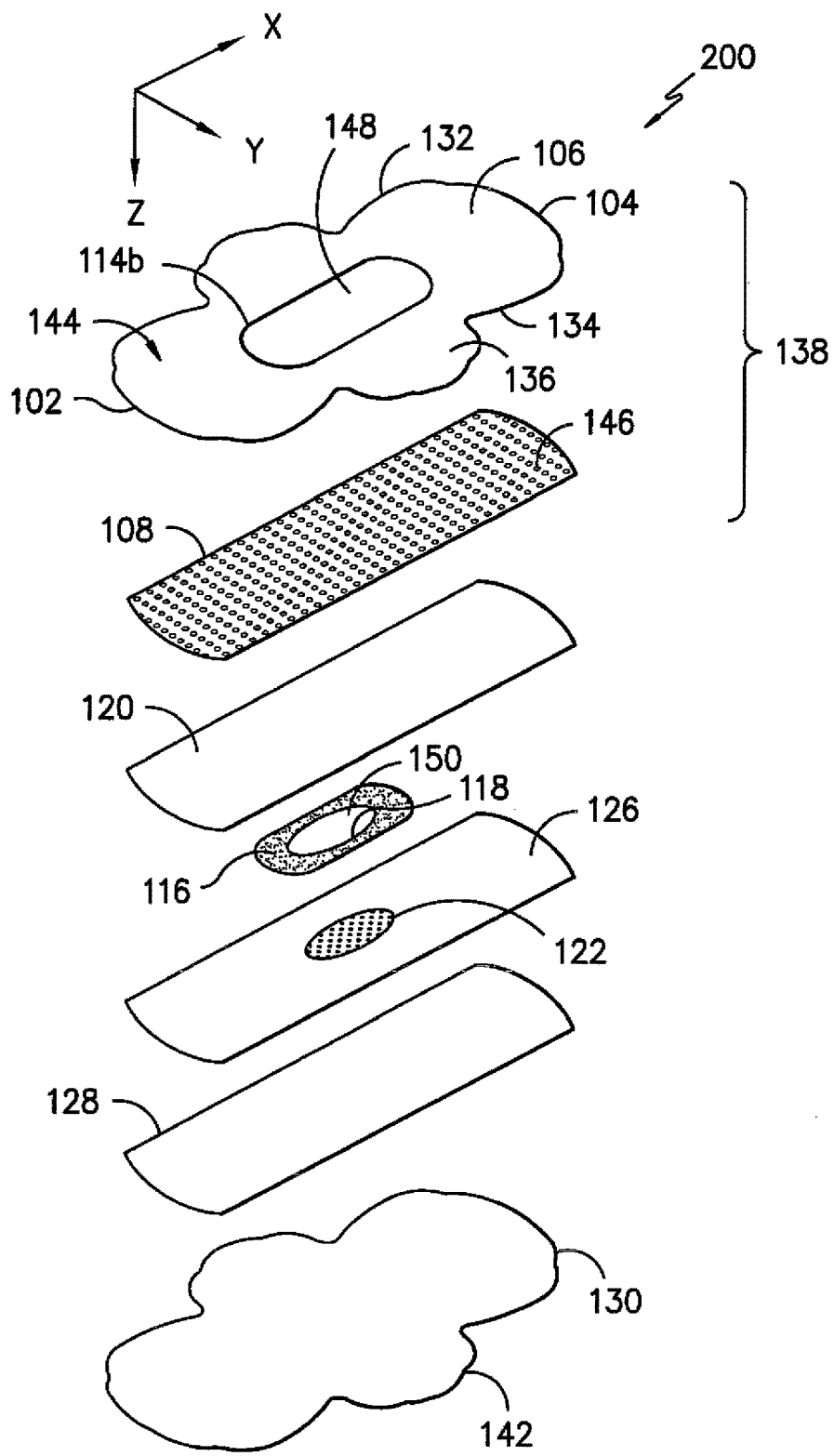
FIG. 6 is an exploded perspective view of FIG. 4.

Generally, the three-dimensional, apertured film that can be used in any layer of the multi-layered topsheet can have an overall thickness between about 5 micrometers and 1000 micrometers, such as from about 10 micrometers to about 500 micrometers, such as from about 25 micrometers to about 250 micrometers. As shown in FIGS. 3, 6, and 10, a plurality of apertures 146 can extend through the first topsheet layer 106 or the second topsheet layer 108 so as to permit fluid flow through the multi-layered topsheet 138. The apertures create passageways through the layers of the absorbent article away from its body-facing surface 144 so that the fluid is received by one or more additional layers through which bodily fluids can flow, such as a first sub-topsheet layer 116 or an absorbent core 128. Further, the apertures 146 may be localized or they may extend across the entire surface of the first topsheet layer 106 or the second topsheet layer 108, which is shown in the embodiment of FIGS. 3 and 6. The number and size of the apertures 146 can be controlled such that the first topsheet layer 106 and/or the second topsheet layer 108 has a percent aperture area due to the presence of the apertures of between about 10% and about 80% based upon the surface area of the first topsheet layer or second topsheet layer, such as from about 15% to about 60%, such as from about 20% to about 40%, excluding the first topsheet layer opening 148 or the second topsheet layer opening 162 (see FIGS. 12 and 13). The percent aperture area is calculated by specifying a unit area, calculating the surface area of the apertures 146 within the specified unit area, dividing this total aperture area by the total surface area within the specified unit area, excluding the first topsheet layer opening 148 or the second topsheet layer opening 162, and then multiplying the quotient by 100 to determine the percent aperture area.

Moreover, it is to be understood that the first topsheet layer 106 and/or the second topsheet layer 108 can be imparted with apertures 146 that have any suitable shape. For instance, the apertures 146 can be hexagonal, circular, ovular, elliptical, polygonal, or any other suitable pattern or combination of shapes. Further, each aperture 146 has an average diameter of from about 50 microns to about 1500 microns, such as from about 100 microns to about 1000 microns, such as from about 200 microns to about 800 microns, where the diameter is large enough to allow insult fluids to be acquired through the three-dimensional, apertured film as rapidly as the fluids are delivered.

In addition, the apertures 146 can be arranged in any suitable pattern to impart the desired amount of stability and fluid transfer properties to the multi-layered topsheet 138. The pattern can also be chosen such that it has an aesthetically pleasing appearance. For instance, in one embodiment, the apertures 146 can be formed in a honeycomb-like, three-dimensional pattern such that the film has sufficient stability to prevent the collapse of the three-dimensional structure during use of the absorbent article, although it is to be understood that other patterns are also useful. The honeycomb pattern of the three-dimensional, apertured film can be imparted onto the film using a metal screen having hexagonal perforations. The materials used to form the film and/or film thickness can be adjusted to provide the desired stiffness and yet also provide the desired softness of the texture of the resulting film as it is used in the multi-layered topsheet 138, which comes into contact with the wearer's skin.

Generally, the three-dimensional, apertured film can be made by any suitable process. For instance, the film can be made by a direct melt vacuum formed film (VFF) process. In the case of a direct melt VFF process, a molten film is extruded onto a forming area of a forming screen. A pressure differential applied across the forming screen causes the molten film to conform to the three-dimensional shape of the forming screen (i.e., a hexagonal shape to form a honeycomb pattern) to form cells that ultimately rupture at their tips to become apertures. Alternatively, the film may be reheated and partially melted while the film is over the forming area of the forming screen. A melted polymer is desirable to form three-dimensional apertures since a melted polymer is more easily pulled into the apertures in a forming screen. The three-dimensional, apertured films of the present invention may also be formed by a hydroformed film (HFF) process. In a HFF process, hydraulic pressure in the form of water jets impinges upon a film as it crosses the forming area of a forming screen. The force of the high-pressure water causes the film to conform to the three-dimensional shape of the forming screen to form cells that ultimately rupture at their tips to become apertures.

Numerous embodiments of the absorbent article of the present disclosure will now be discussed in more detail. As shown in FIGS. 1, 3, 4, 6, 12, 13, 21, and 23, the multi-layered topsheet 138 defines a body-facing surface 144 of the absorbent article and includes a first topsheet layer 106 that is disposed above the second topsheet layer 108 in the z-direction, which is thus disposed below the first topsheet layer 106 in the z-direction. The first topsheet layer 106 can include any of the topsheet materials discussed above, and the first topsheet layer 106 can also include a combination of any of these materials, such as in a laminate form.

The dimensions of the first topsheet layer 106 can vary depending on the particular need for which the absorbent article is being used. Generally, the length of the first topsheet layer 106 in the longitudinal (x) direction is from about 100 millimeters (mm) to about 450 mm, such as from about 150 mm to about 400 mm, such as from about 200 mm to about 380 mm. Further, the width of the first topsheet layer 106 in the transverse (y) direction (excluding any optional wings) is from about 60 mm to about 200 mm, such as from about 70 mm to about 175 mm, such as from about 80 mm to about 150 mm. Further, the first topsheet layer 106 can have a basis weight up to about 50 gsm, such as from about 10 gsm to about 40 gsm. The first topsheet layer 106 defines the body-facing surface 144 of the absorbent article and because of the material from which it is formed, can provide for a soft, comfortable material against the skin of the wearer.

As shown at least in FIGS. 1-9, 11-13, and 20-23, the first topsheet layer 106 also defines an opening 148 having a perimeter 114a, 114b, or 114c. The perimeter 114a, 114b, or 114c forms the inner border or inner edge of the first topsheet layer 106, leaving an opening 148 through which at least a portion of the second topsheet layer 108 can be exposed and visible due to the lack of presence of the first topsheet layer 106 at the opening 148, as shown in FIGS. 3, 6, 12, 14-17, 23-27. However, it is also to be understood that in some embodiments, such as in FIG. 13, the second topsheet layer 108 may not be exposed at the opening 148 if the second topsheet layer opening 162 is larger than the first topsheet layer opening 148. In any event, the opening 148 in the first topsheet layer 106 helps to direct bodily fluids away from the body of the wearer and toward an absorbent layer in the absorbent article, such as the sub-topsheet layer 116, which is disposed below the first topsheet layer 106 in the z-direction. The opening 148 also permits the multi-layered topsheet 138 to bend and conform to the wearer's body to prevent leakage of fluids due to the formation of peaks and valleys in the multi-layered topsheet upon the introduction of compressive forces.

The first topsheet layer opening 148 in FIGS. 1-9 and 11-27 can be located at various positions along the longitudinal and transverse directions of the first topsheet layer 106 depending on the primary location of fluid intake or the purpose for which the absorbent article is being used. For instance, in the embodiment shown in FIGS. 1 and 4, the first topsheet layer opening 148 is positioned so that it is in substantial alignment with the longitudinal centerline $C_L$ and the transverse centerline $C_T$. It should be understood that the longitudinal centerline $C_L$ is disposed at a location that is equidistant from the first edge 132 and second edge 134 and runs along the length of the first topsheet 106 in the longitudinal (x) direction, while the transverse centerline $C_T$ is disposed at a location that is equidistant from the distal end 102 and proximal end 104 and runs along the width of the first topsheet 106 in the transverse (y) direction. This configuration allows the opening 148 to be centrally disposed so that it can be positioned below the main point of fluid discharge and so that it can act as the primary fluid-receiving area for the multi-layered topsheet 138. Thus, the first topsheet layer opening 148 can be used in directing bodily fluids towards a central location in the absorbent article away from the body-facing surface 144 of the absorbent article in the z-direction, which can reduce the risk of leakage of the fluids when a fluid insult occurs at a central location on the absorbent article 100 or 200.

Figure 7:
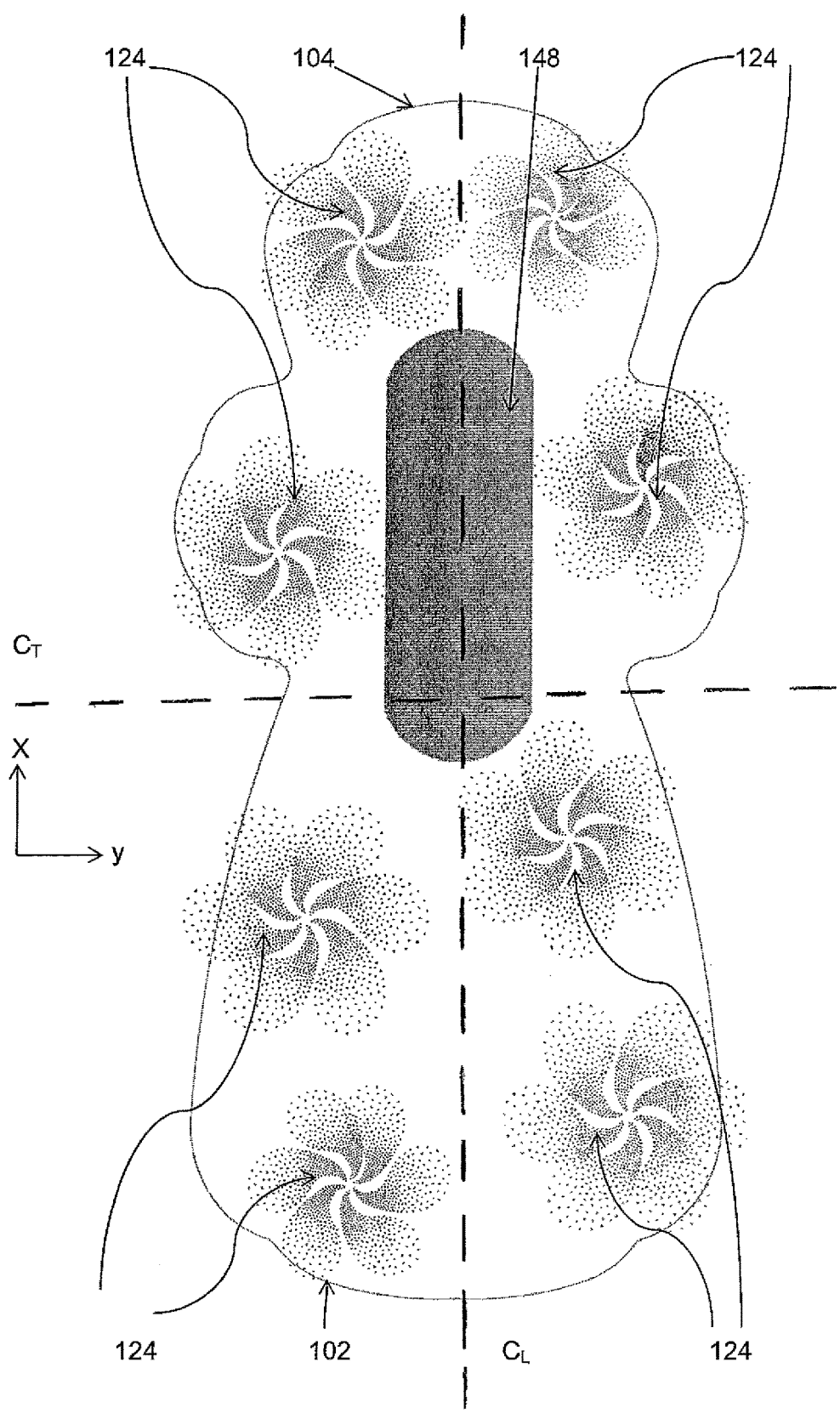
FIG. 7 is a top view of one embodiment of the absorbent article of the present invention.

However, centralized positioning of the first topsheet layer opening 148 is not required, and in some embodiments, depending on the primary location where fluid intake may occur, the opening 148 may be substantially aligned with the longitudinal centerline $C_L$ only. Thus, the first topsheet layer opening 148 may be shifted in the longitudinal (x) direction towards either the distal end 102 or proximal end 104 of the first topsheet layer 106 so that the first topsheet layer opening 148 is not in substantial alignment with the transverse centerline $C_T$ as shown in FIGS. 7 and 11. Such particular embodiments are discussed in more detail below.

For instance, the first topsheet layer opening 148 can be shifted towards the proximal end 104 of the first topsheet layer 106 such that the center of the opening 148 is not substantially aligned with the transverse centerline $C_T$ of the absorbent article in the longitudinal (x) direction, although the opening 148 is substantially aligned with the longitudinal centerline $C_L$ in the transverse (y) direction. In another embodiment (not shown), the opening 148 defined by perimeter 114a or 114b can be shifted toward the distal end 102 of the absorbent article, again depending on the primary location where fluid intake may occur.

Figure 2:
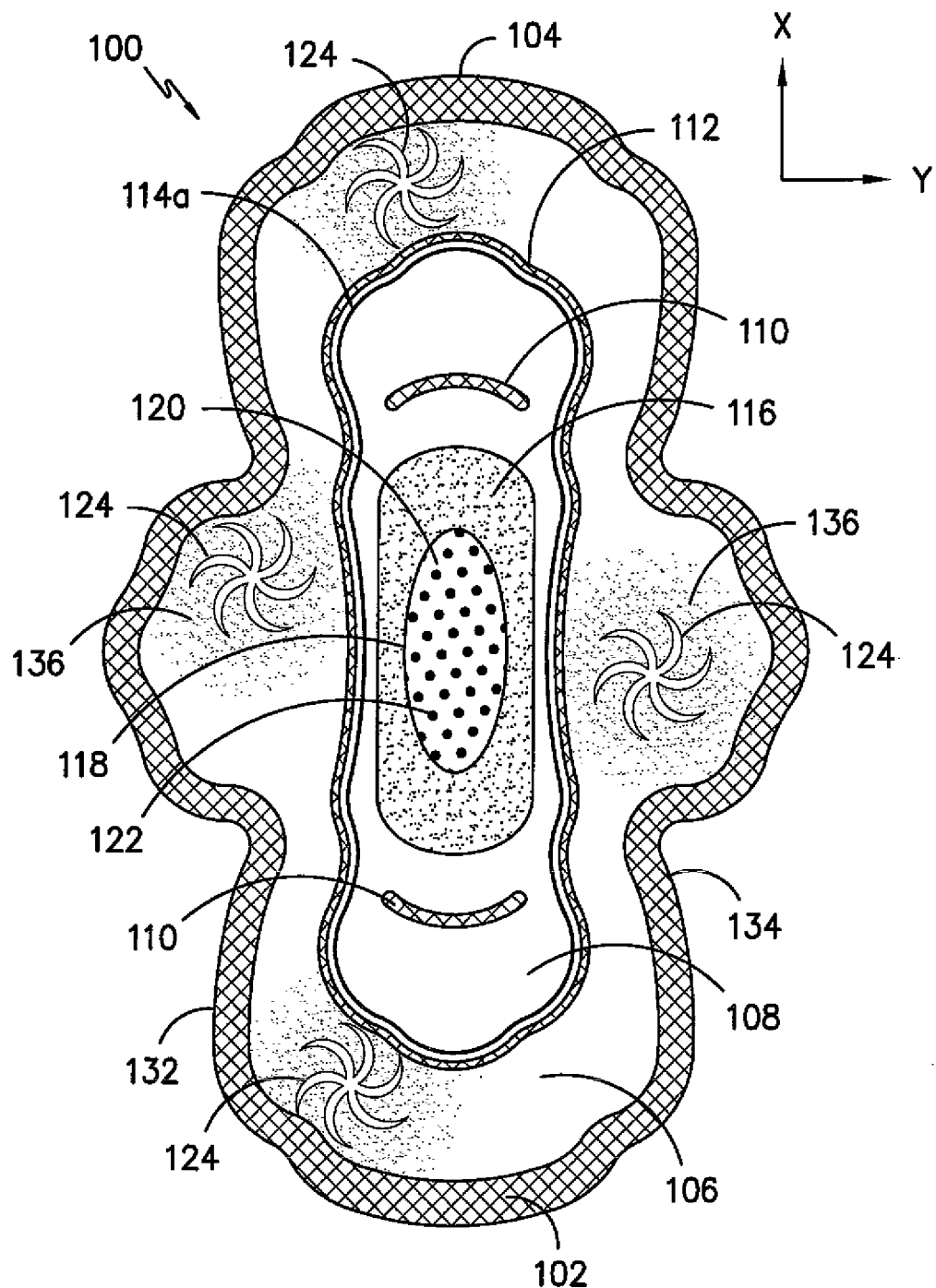
FIG. 2 is a top view of FIG. 1.

Generally, the first topsheet layer opening 148 can either have a closed complex or simple shape based on the shape of the perimeter 114a, 114b, or 114c, for example. For instance, the perimeter can be a complex shape, such as the perimeter 114a of FIG. 1-3 or 114c of FIGS. 20-23. Perimeter 114a of FIGS. 1-3 is a complex shape that is generally oblong and is defined as having one or more protrusions, such as multiple protrusions 184 located along the longitudinal (x) direction and multiple protrusions 186 located along the transverse (y) direction. The presence of the protrusions 184 and 186 in the perimeter 114a results in a first topsheet layer opening 148 that has corresponding protrusions, and these protrusions allow the first topsheet layer 106 to bend and conform to the crotch region of the wearer's body, which can provide a close fit and prevent compressive forces from forming peaks and valleys in the absorbent article, which can lead to pooling and leakage. Meanwhile, perimeter 114c of FIGS. 20-23 is also a complex shape, and in this instance, the perimeter 114c has a protrusion 184 located along the longitudinal (x) direction towards the first edge 132 and another protrusion 184 located along the longitudinal (x) direction towards the second edge 134 of the absorbent article. These two protrusions 184 create an opening 148 having corresponding bulges along the transverse (y) direction. It should be noted that a larger number of protrusions, such four or more, six or more, or eight or more may be required in perimeter 114a to allow first topsheet layer 106 to bend sufficiently to conform to the wearer's body, while perimeter 114c may require two protrusions to allow the first topsheet layer 106 to bend sufficiently to conform to the wearer's body because of the smaller opening 148 formed by perimeter 114c.

In any event, the perimeter 114a or 114c can form an opening 148 that has a length in the longitudinal (x) direction that is from about 50 mm to about 300 mm, such as from about 75 mm to 275 mm, such as from about 100 mm to about 250 mm. The perimeter 114a or 114c can also form an opening 148 that has a width in the transverse (y) direction at its widest point that is from about 20 mm to about 100 mm, such as from about 25 mm to about 90 mm, such as from about 30 mm to about 80 mm. Further, the opening 148 defined by perimeter 114a or 114c can have a length that is from about 15% to about 80%, such as from about 20% to about 75%, such as from about 25% to about 70% of the overall length of the first topsheet layer in the longitudinal (x) direction. The opening 148 defined by perimeter 114a or 114c can also have a width that is from about 20% to about 80%, such as from about 25% to about 75%, such as from about 30% to about 70% of the overall width of the first topsheet layer in the transverse (y) direction, excluding any optional wing portions.

Figure 4:
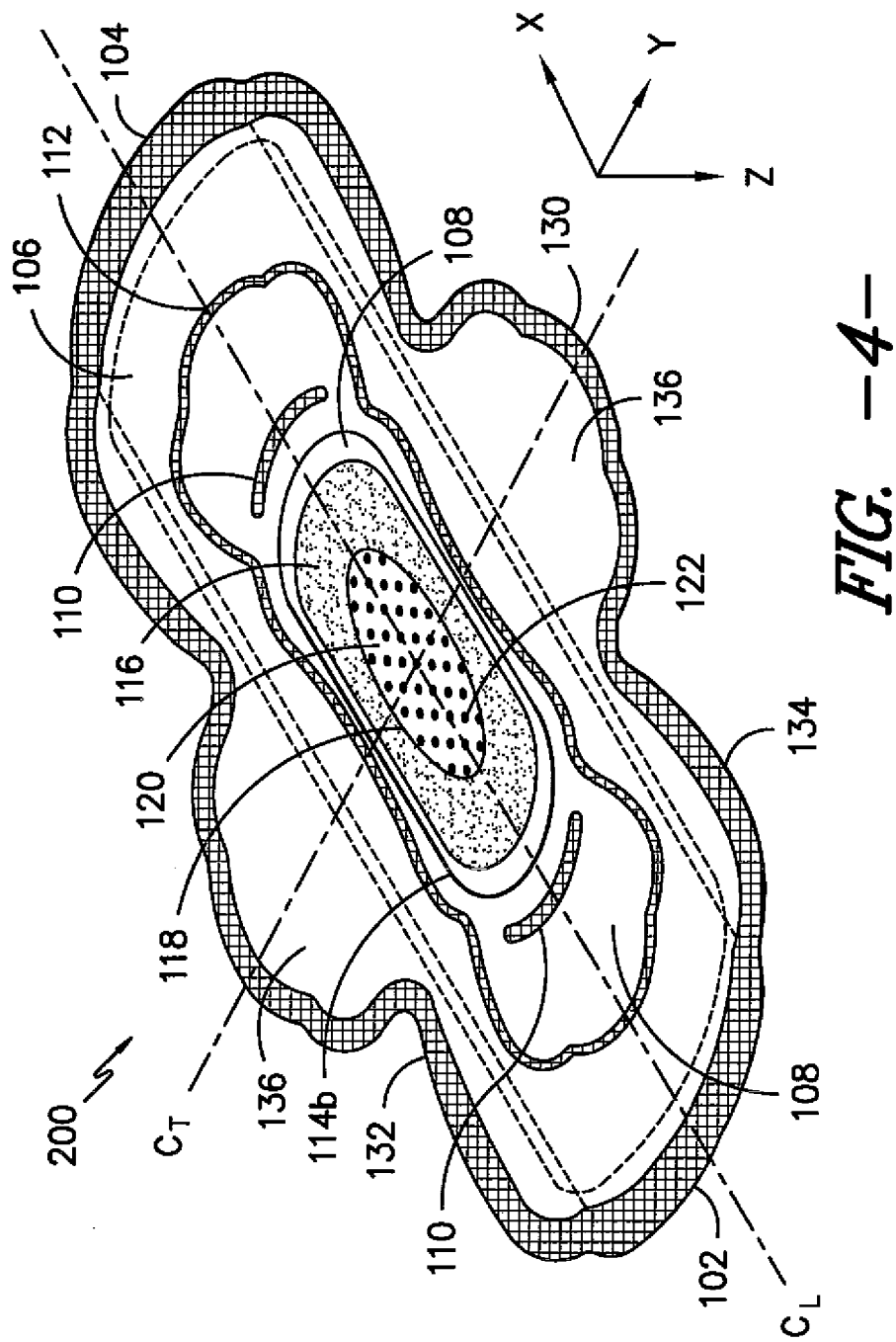
FIG. 4 is a perspective view of another embodiment of the absorbent article of the present invention.
Figure 5:
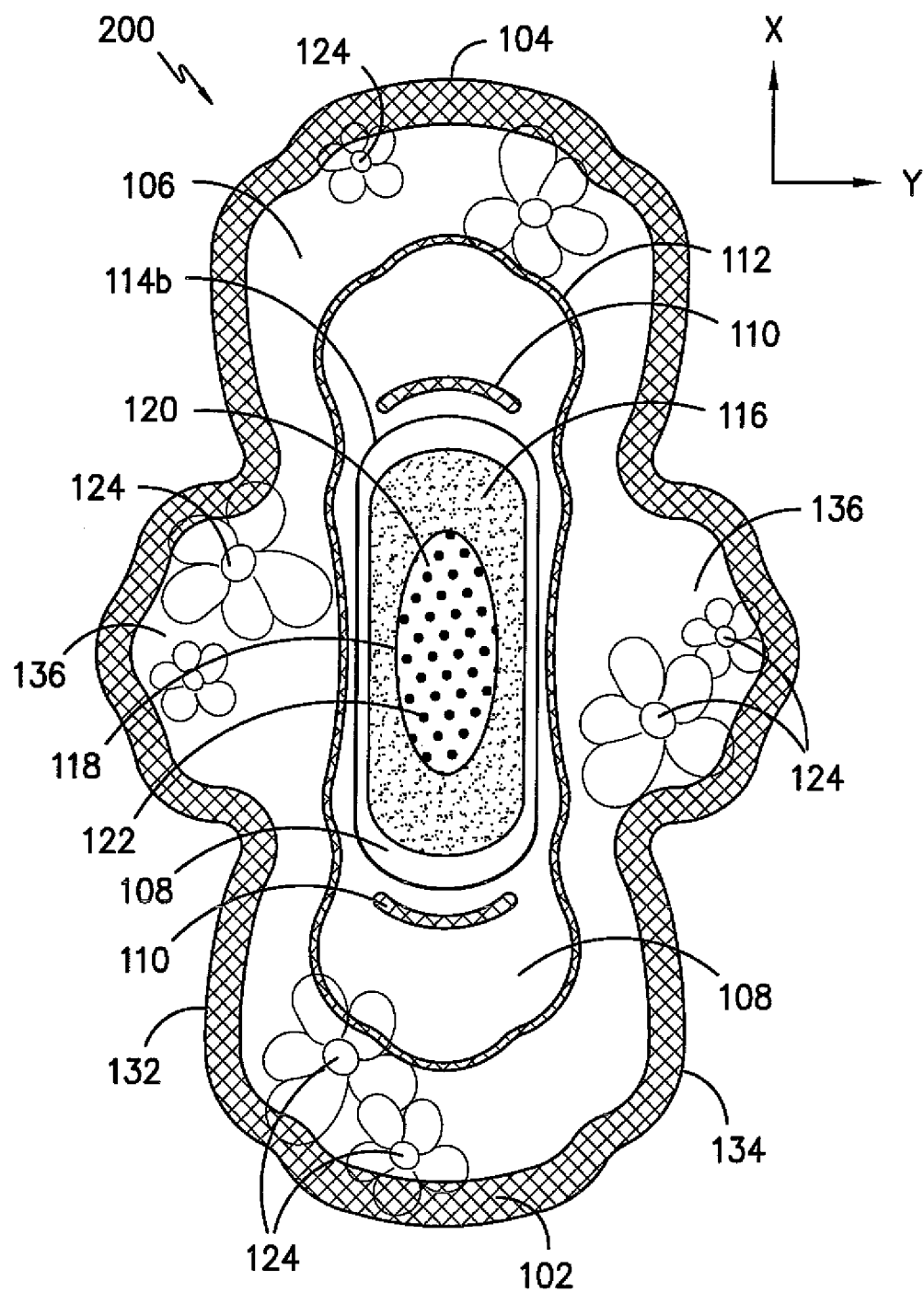
FIG. 5 is a top view of FIG. 4.

Meanwhile in the embodiment of FIGS. 4-6, perimeter 114b has a more simplistic shape, and specifically has a smaller, smooth, substantially ovular shape when compared to perimeters 114a and 114c. More specifically, the shape of the perimeter 114b can be described as a rectangle having semi-circular ends or as a race-track shape. Unlike perimeter 114a or perimeter 114c, perimeter 114b lacks protrusions, as its smaller dimensions mean that it does not need to bend to help it shape and conform against the body. Generally, the perimeter 114b can form an opening 148 that has a length in the longitudinal (x) direction that is from about 25 mm to about 200 mm, such as from about 50 mm to 175 mm, such as from about 75 mm to about 150 mm. The perimeter 114b can also form an opening 148 that has a width in the transverse (y) direction that is from about 20 mm to about 100 mm, such as from about 25 mm to about 90 mm, such as from about 30 mm to about 80 mm. Further, the opening 148 defined by perimeter 114b can have a length that is from about 15% to about 80%, such as from about 20% to about 75%, such as from about 25% to about 70% of the overall length of the first topsheet layer in the longitudinal (x) direction. The opening 148 defined by perimeter 114b can also have a width that is from about 20% to about 80%, such as from about 25% to about 75%, such as from about 30% to about 70% of the overall width of the first topsheet layer in the transverse (y) direction, excluding any optional wing portions.

Although perimeter 114a, perimeter 114b, and perimeter 114c are generally shown in FIGS. 1-9 and 20-23 as a complex oblong shape having multiple protrusions (FIGS. 1-3), a more simplistic, substantially ovular shape (FIGS.

4-9), or a complex shape that is generally ovular but has protrusions to form two bulges in the absorbent article (FIGS. 20-23), the perimeter 114*a*, 114*b*, or 114*c* can be any suitable shape as is required to create an opening 148 that can draw or direct bodily fluids away from the skin of the wearer and hold the fluids while such fluids are being transferred away from the body-facing surface 144 of the absorbent article and towards various lower layers of the absorbent article in the z-direction. The shape of the perimeter and opening it defines can also provide a visual cue to the wearer to assist in the proper placement of the absorbent article. For instance, the perimeters 114*a* and 114*b* can be rectangular, square, circular, elliptical, dog-bone, triangular, or diamond shaped.

Moreover, as shown in FIG. 11, when the first topsheet layer opening 148 is shifted towards the proximal end 104 of the first topsheet layer 106 as mentioned above, a distal end first topsheet layer opening 164 defined by distal end perimeter 166 can be present towards the distal end 102 of the first topsheet layer 106. In particular, the absorbent article 300 of FIG. 11 can be used as an overnight pad, and can provide additional protection from staining of clothing or bedding during overnight use of the absorbent article due to the presence of two discrete openings 148 and 164 in the first topsheet layer 106 that can direct fluid flow to different locations in the absorbent layers of the article. Such overnight pads are often designed with extended lengths so as to provide coverage for the vaginal area (towards proximal end 104) and buttocks area (towards distal end 102) during sleep. Often such pads include a wider distal end area so as to thoroughly cover the buttocks region.

It is to be understood that although distal end first topsheet layer opening 164 is shown in FIG. 11 as having a simple, generally ovular shape, the opening 164 can be of any suitable shape as discussed above in reference to first topsheet layer opening 148, such as a complex shape. Further, it is to be understood that the perimeters 114*a*, 114*b*, 114*c*, and 166 can be formed by any suitable method to form an opening 148 or 164 in the first topsheet layer 106, such as by knife cutting, laser cutting, or die cutting.

Additionally, no matter the shape or size of the opening 148 formed by perimeter 114*a*, 114*b*, or 114*c*, at least a portion of the first topsheet layer 106 material is present from the perimeter 114*a*, 114*b*, or 114*c* of the first topsheet layer 106 to the outer periphery of the absorbent article toward the distal end 102, proximal end 104, first edge 132, and second edge 134. Additionally, at least a portion of the first topsheet layer 106 material is present from the distal end perimeter 166 of the first topsheet layer 106 to the outer periphery of the absorbent article toward the distal end 102, proximal end 104, first edge 132, and second edge 134. Thus, the first topsheet layer 106 is positioned above the second topsheet layer 108 in the z-direction so that the second topsheet layer 108 is only exposed, if at all, at the opening 148 defined by perimeter 114*a* or 114*b* or optional opening 164 of the first topsheet layer 106.

Because of the configuration of the multi-layered topsheet 138 discussed above in which the first topsheet layer 106 completely surrounds the second topsheet layer 108, at least one printed graphic 124 can be printed at any location near the periphery of the absorbent article on the first topsheet layer 106, although such printing is not required. Moreover, it is to be understood that printed graphics 124 can be printed on either the body-facing surface 144 of the absorbent article as defined by the first topsheet layer 106 or an opposing inwardly-facing surface of the first topsheet layer 106 that faces the baffle or other lower layers of the absorbent article in the z-direction. Further, the printed graphics 124 can be printed on any other layer of the multi-layered topsheet 138 and on any surface provided that the printed graphics 124 are visible from the body-facing surface 144 of the absorbent article. In addition, the printed graphics 124 can be printed on layers besides or in addition to the multi-layered topsheet 138, such as a surge layer, distribution layer, transfer layer, intake layer, absorbent layer, etc., so long as the printed graphics 124 are visible from the body-facing surface 144 of the absorbent article. When the printed graphics 124 are visible from the body-facing surface 144 of the absorbent article, the overall aesthetic look of the absorbent article can be enhanced. In addition, the printed graphics 124 can also function to mask visible stains on the absorbent article and can be used in conjunction with any of the openings in the various layers of the absorbent article to provide a visual cue as to the proper placement of the absorbent article, as the printing around the opening 148 or 164 can make the opening more visible.

For instance, at least one printed graphic 124 can be visible from the body-facing surface 144 of the absorbent article and can be printed from the perimeter 114*a*, 114*b*, or 114*c* of the opening 148 to the periphery of the absorbent article at each of the distal end 102, proximal end 104, first edge 132, and second edge 134. As shown in FIGS. 2, 5, and 7-9, the printed graphics 124 can be of any aesthetically pleasing pattern. Further, the printed graphics 124 can be multicolored. Additionally, it should be understood that the printed graphics 124 can be printed on any surface of the first topsheet layer 106, such as the surface that defines the body-facing surface of the absorbent article, or the surface that is contact with the second topsheet layer 108. Further, if the first topsheet layer 106 itself includes multiple layers or types of materials, the printed graphics 124 can be printed on any layer or material so long as the printed graphics 124 are visible from the body-facing surface 144 of the absorbent article, as defined by the first topsheet layer 106.

Figure 8:
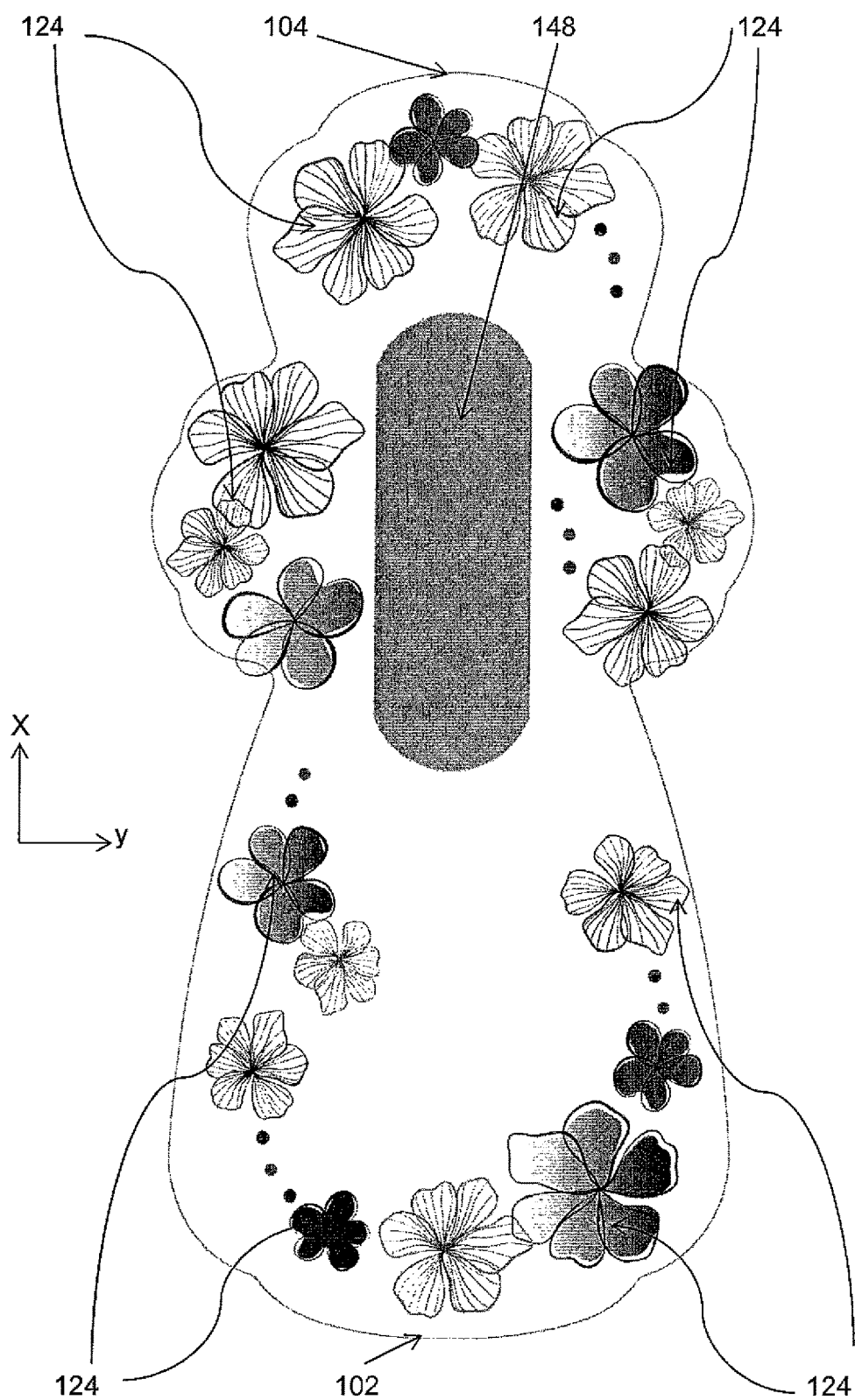
FIG. 8 is a top view of another embodiment of the absorbent article of the present invention.
Figure 9:
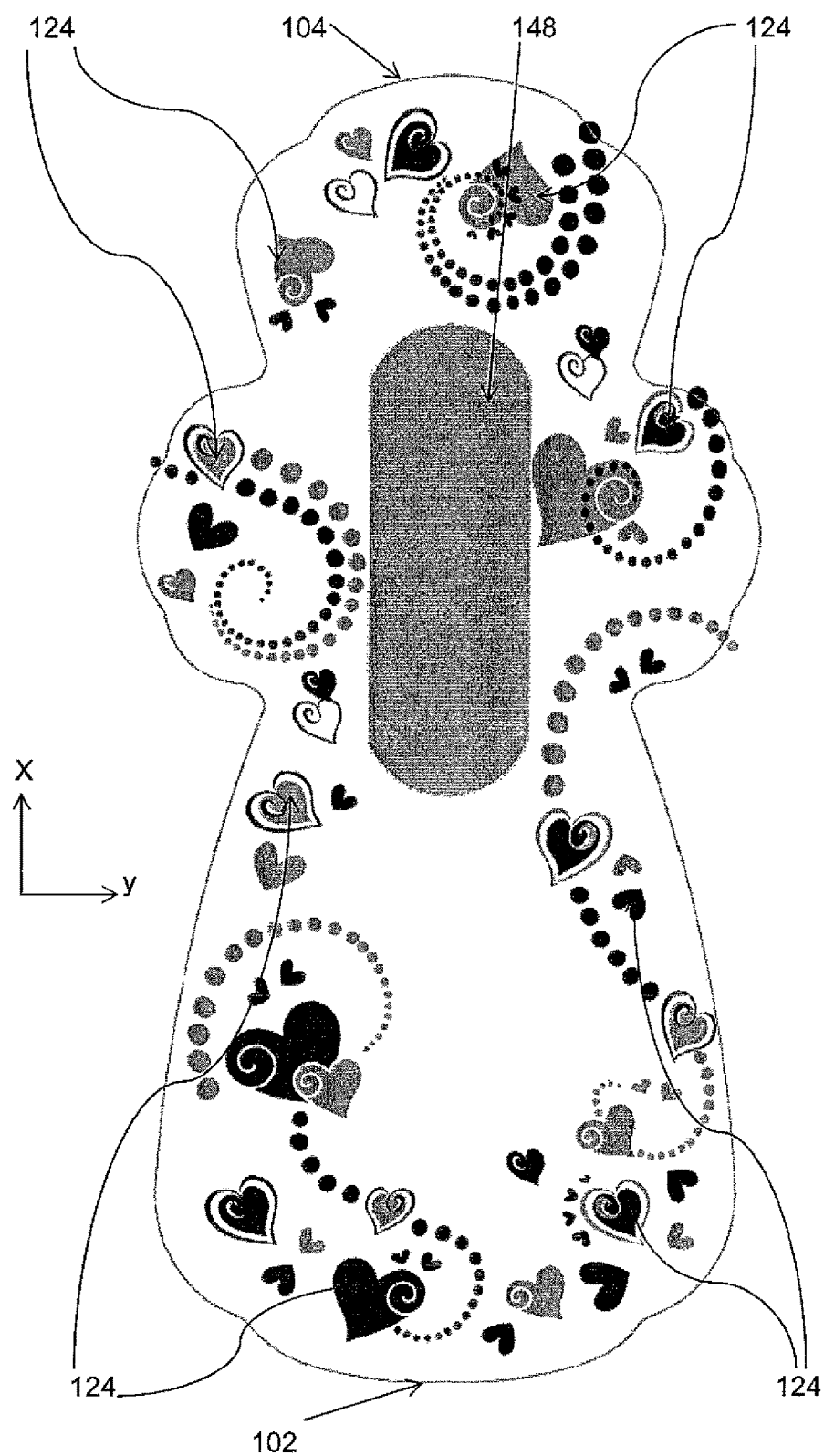
FIG. 9 is a top view of still another embodiment of the absorbent article of the present invention.

Moreover, the printed graphics 124 can be symmetrical or asymmetrical about a central axis in the longitudinal (x) direction, the transverse (y) direction, or both through the use of objects of different sizes, colors, shapes, and designs. In the embodiments of FIGS. 7-9, for example, the asymmetrical nature of the printed graphics 124 can allow the color or stain of the bodily fluid to better blend with the visual nature of the patterns, and also draws the wearer's focus away from the areas in which any stains may be visible, such as at the first topsheet layer opening 148.

Asymmetry in the printed graphics 124 described above may be provided in a variety of ways, such as through the use of printed graphics 124 having different sizes, colors, shapes, and designs. Such asymmetry accomplishes the dual functions of providing a unique and distinctive "pre-use" visual appearance, and providing a "post-use" visual appearance that can mask stains after the product has been used. The asymmetry indicates that the patterns do not have simple symmetry like reflection, rotational, and translational symmetries, and preferably do not have glide reflection, roto-reflection, helical, or non-isometric symmetries. While being asymmetrical, the patterns may nevertheless provide an asymmetrical balance to the extent that several smaller graphical objects on one side may be "balanced" by a large graphical object on the other side, or smaller objects may be placed further away from the center than larger objects. Alternatively, a darker object may be similarly balanced by several lighter objects. It also should be noted that although the printed graphics 124 of FIGS. 2 and 5 are shown herein as possessing relatively simple shapes, this is merely for exemplary purposes. However, virtually any shape or design may be employed, such as dots, ovals, triangles, squares, rectangles, flowers, butterflies, stars, hearts, pinwheels, spirals, double spirals, clothoid curves, cornu spirals, polynomial double spirals, Euler's double spirals, parametric double spirals, paisley, etc. In fact, it is generally preferable that the graphical objects are more complicated in nature and that they possess some degree of curvature and color to provide a more complex visual perception and aid in the overall masking effect of the article. For example, FIGS. 7-9 generically illustrate more complex graphical objects that may be employed in the present invention.

The specific printed graphics 124 may also be selected so that, although asymmetrical, they are visually coordinated with the surrounding environment to provide a perception that the product will perform better. The surrounding environment may, for instance, be the packaging (e.g., wrapper, bag, etc.) within which the absorbent article is initially provided, such as described in U.S. Patent Publication No. 2005/0154365 to Zander, et al., which is incorporated herein in its entirety by reference thereto for all purposes. The objects may also be visually coordinated with a garment, such as described in U.S. Patent Publication No. 2008/0058748 to Seifert, et al., which is also incorporated herein in its entirety by reference thereto for all purposes. Visually coordinated graphical objects are those in which two or more visual characteristics either match or are caused to match.

In certain cases, the printed graphics 124 may be arranged to impart an optical illusion when viewed from a particular focal point of the user. For instance, the arrangement of the graphical objects relative to one another may form an optical illusion of motion perceivable as at least one of the objects appearing to move away from an edge of the body. Exemplary objects for providing such an illusionary pattern may include geometric, spiral, anomalous motion, rotational, color change, peripheral drift, positive after image blurs, scintillation grid, stereopsis and chromosteropsis, contraction and expansion, contrast polarities, convection, chromatic assimilation, etc., such as described in U.S. Patent Publication No. 2009/0157021 to Sullivan, et al., which is incorporated herein in its entirety by reference thereto for all purposes. In another embodiment, graphical objects of different shades may be employed. Regardless of the mechanism employed, the optical illusions can cause the wearer to perceive the stain to be different in the product than it actually is, thus enhancing the masking of the stain.

The printed graphics 124 can be printed onto the absorbent article by any suitable method. For instance, offline printing can be used to print the graphics 124 onto the first topsheet layer 106 prior to forming the opening 148 in the first topsheet layer 106. Additionally, various colors of ink can be used to form the printed graphics 124 on the desired layer of the absorbent article, such as one or more colors.

To print the printed graphics 124 on the first topsheet layer 106 or any other suitable layer of the absorbent article so long as the printed graphics can be visible from the body-facing surface of the absorbent article, various types of printing processes can be utilized, such as stencil and screen printing, relief printing, planographic printing, intaglio printing, and electronic printing. Examples of relief printing may include letterpress and flexography. Examples of planographic printing may include offset lithography, screenless lithography, collotype, and waterless printing. In addition, examples of intaglio printing may include gravure, steel-die, and copper-plate engraving. Examples of electronic printing may include electrostatic, magnetographic, ion or electron deposition, and ink-jet printing.

In addition to the aforementioned various types of printing processes, it is to be understood that various types of inks or ink systems may be applied to the absorbent article to create the described printed graphics 124, such as solvent-based, water-based, and UV-cured inks.

Moreover, besides a first topsheet layer 106 which has been discussed in detail above, the multi-layered topsheet 138 also includes a second topsheet layer 108 that is situated beneath and can be in direct contact with the first topsheet layer 106, although it is to be understood that in some instances, another layer of the absorbent article can be disposed between the first topsheet layer 106 and the second topsheet layer 108 in the z-direction. As shown in the particular examples of FIGS. 3 and 6, the second topsheet layer 108 can be a liquid permeable three-dimensional, apertured film. However, it is to be understood that the second topsheet layer 108 can include any of the other suitable topsheet materials discussed above, and the second topsheet layer 108 can also include a combination of any of these materials. In some embodiments, the second topsheet layer 108 is typically situated beneath the first topsheet layer 106 and above a sub-topsheet layer 116 and any other layer that may be disposed between the baffle 130 and the second topsheet layer 108 in the z-direction, such as one or more surge layers, transfer layers, distribution layers, intake layers, absorbent core layers, or additional topsheet layers.

In addition to being formed from, for instance, a nonwoven material or a film, the second topsheet layer 108 can be cut into any suitable size and shape based on the need of the particular absorbent article in which it is being used. In one embodiment, the second topsheet layer 108 can extend across the entire absorbent article in the longitudinal and transverse directions, such that it has the same overall dimensions as the first topsheet layer 106. However, it is also to be understood that the second topsheet layer 108 may not extend to wing portions 136, and the second topsheet layer 108 may have a smaller overall length in the longitudinal direction (x) and a smaller overall width in the transverse (y) direction than the first topsheet layer 106, as shown in FIGS. 3 and 6. For instance, the overall length of the second topsheet layer 108 can be from about 30% to about 100% of the overall length of the first topsheet layer 106, such as from about 40% to 99% of the overall length of the first topsheet layer 106, such as from about 50% to about 98% of the overall length of the first topsheet layer 106. Further, the overall width of the second topsheet layer 108 can be from about 10% to about 100% of the overall width of the first topsheet layer 106, such as from about 25% to about 99% of the overall width of the first topsheet layer 106, such as from about 50% to about 98% of the overall width of the first topsheet layer 106.

Moreover, like the first topsheet layer 106, the second topsheet layer 108 of the absorbent article of the present disclosure can also have an opening to contribute to the funnel-like effect exhibited by the absorbent article after a fluid insult, although this is not required. FIGS. 1-6, 21, and 23 show an absorbent article where the second topsheet layer 108 does not have an opening such that the second topsheet layer 108 is exposed at the first topsheet layer opening 148, while FIGS. 12-13 show an absorbent article where the second topsheet layer 108 does have an opening 162. As shown in absorbent article 400 of FIG. 12, the second topsheet layer opening 162, as defined by perimeter 160a, can be smaller than the first topsheet layer opening such that when the second topsheet layer opening 162 is situated below the first topsheet layer opening 148, a portion of the second topsheet layer remains exposed. However, in another embodiment, as shown in absorbent article 500 of FIG. 13, the second topsheet layer opening 162, as defined by perimeter 160b, can be larger than the first topsheet layer opening 148 such that when the second topsheet layer opening 162 is situated below the first topsheet layer opening 148, the second topsheet layer 108 is not exposed. In addition, the aforementioned second topsheet layer openings can be complex shapes with protrusions or simple shapes without protrusions, as discussed in more detail above in reference to the first topsheet layer opening 148. Generally, the topsheet layer openings, whether present in both the first and second topsheet layers, or just one of the layers, function to draw bodily fluids away from the skin of the wearer and isolate the fluids in a desired location in a lower level of the absorbent article in the z-direction. The openings also permit the absorbent article to bend and conform to the wearer's body to prevent pooling of fluids in channels that may be created in the absence of such openings due to compressive forces exerted on the absorbent article. When both the first topsheet layer 106 and the second topsheet layer 108 include openings 148 and 162, a third topsheet layer 182 lacking an opening can be disposed between the second topsheet layer 108 and the baffle in the z-direction of the absorbent article, as shown in FIGS. 12-13. In this manner, the wearer's body can be in contact with a topsheet layer material which provides softness and is comfortable against the skin of the wearer.

Whether the second topsheet layer 108 is continuous as in FIGS. 3, 6, 21, and 23 or has an opening 162 situated beneath the first topsheet layer opening 148 that is smaller than the first topsheet layer opening 148 as shown in FIG. 12 such that the perimeter 160a is substantially surrounded or framed by the perimeter 114a when viewed from body-facing surface 144 of the absorbent article in the z-direction, the second topsheet layer 108 can be joined to the first topsheet layer 106 by a seal that is formed around the first topsheet layer opening 148 at or near perimeter 114a, 114b, or 114c and generally corresponds with the shape of the perimeter 114a, 114b, or 114c. Thus, the seal can be generally concentric with the perimeter 114a, 114b, or 114c. The seal can also be a generally continuous seal around the perimeter 114a, 114b, or 114c. In the embodiments of absorbent articles 100, 400, 900, and 1000, as shown in FIGS. 1-3, and 12, the seal generally corresponds with the complex shape of the perimeter 114a of opening 148 which has multiple protrusions 184 and 186 in the longitudinal (x) and transverse (y) directions. The seal can also generally correspond with the shape of embossed region 112, as discussed in more detail below. Meanwhile, in the embodiment of absorbent article 200 shown in FIGS. 4-6, the seal generally corresponds with the shape of the perimeter 114b of opening 148, which is generally in the shape of an oval or a rectangle having semi-circular ends. Further, in the embodiments of absorbent articles 900 and 1000 shown in FIGS. 20-23, the seal generally corresponds with the shape of perimeter 114c of opening 148, which generally has two bulges formed by protrusions 184 located in the longitudinal (x) direction. Thus, the seal is generally concentric with perimeter 114a, 114b, or 114c. On the other hand, if the second topsheet layer opening 162 is larger than the first topsheet layer opening 148 such that the perimeter 114b is substantially surrounded by perimeter 160b as shown in absorbent article 500 of FIG. 13, then the seal generally corresponds with the shape of the perimeter 160b of the second topsheet layer opening 162. Thus, the seal can be generally concentric with the perimeter 160b. The seal can also be a generally continuous seal around the perimeter 160b.

Further, the seal is formed in such a manner that the area at which the two layers are sealed has the appearance and feel of a single, continuous layer instead of two separate layers that have been sealed together. This improves the comfort of the wearer, as the transition from the first topsheet layer 106 to the second topsheet layer 108 is smooth. Further, the transition area where the two layers are sealed is visually appealing because the first topsheet layer 106 and second topsheet layer 108 appear as if they are in the same plane even though the first topsheet layer 106 is disposed above the second topsheet layer 108. The seal can be formed by methods known to those of ordinary skill in the art, such as via an adhesive, pressure, heat, ultrasonic bonding, or combinations thereof.

Additional features can also be incorporated into the multi-layered topsheet 138 of the absorbent article to enhance the aesthetic appearance of the absorbent article and to reduce the likelihood of leakage upon a fluid insult to enhance the aesthetic appearance of the absorbent article. For instance, lateral strips that run along the absorbent article in the longitudinal (x) direction can be applied above the first topsheet layer 106 at the body-facing surface 144 of the absorbent article. Because the lateral strips are generally applied above the first topsheet layer, the lateral strips become a part of the body-facing surface 144 of the absorbent article. These strips can be formed of any suitable topsheet material and can further prevent leakage of fluid at the peripheral edges of the absorbent article in the transverse (y) direction.

Further, one or more embossed regions can be formed in one or more layers of the multi-layered topsheet 138. Generally, the one or more embossed regions can be described as channels formed in the multi-layered topsheet 138 due to deformation of the multi-layered topsheet 138. The embossed regions are formed in any suitable pattern to not only create an aesthetically pleasing surface, but also to facilitate intake of bodily fluids in that the fluid will tend to flow along the densified edges of the channels rather than pool on contact points of the multi-layered topsheet 138. The embossed regions can also assist in funneling bodily fluids toward a desired location in the absorbent article. The embossed regions may also improve the consistency of the fit properties of the article, both before and after a fluid insult. To provide the absorbent article with such characteristics, the embossed channels may be positioned towards the periphery of the multi-layered topsheet 138 in either a symmetric or asymmetric manner.

Further, the embossed regions may be formed using any known conventional techniques known in the art. Suitable techniques include, for instance, the use of raised elements to impart the desired embossing pattern to create compressed channels in the multi-layered topsheet 138. For instance, a suitable process may involve thermal bonding wherein a layer is passed through two rolls (e.g., steel, rubber, etc.) where one is engraved with an embossing pattern and the other is flat. One or both rolls may be heated. In addition, thermal and/or ultrasonic bonding techniques may be employed for to create the embossed regions.

As discussed above, at least one embossed region can be present on the multi-layered topsheet 138 of the absorbent article of the present disclosure. In the embodiments shown in FIGS. 1-2, 4-5, 11, 20, and 22, this region is shown as embossed region 112. Further, embossed region 112 is present over both the first topsheet layer 106 and the second topsheet layer 108 of the multi-layered topsheet 138 no matter the shape of the opening 148 defined by perimeter 114a, 114b, or 114c. This configuration has an aesthetically pleasing appearance and provides a certain topography to the absorbent article to direct fluid to a desired location and prevent leakage and/or pooling of the fluid around the edge of the absorbent article.

Generally, the embossed region 112 can mask the appearance, if any, of the seal between the two topsheet layers 106 and 108, and it also functions to provide support and structure to the multi-layered topsheet 138 near the seal. Embossed region 112 can generally extend around the entire absorbent article in a complex, oblong shape that has numerous protrusions along the longitudinal (x) direction and/or transverse (y) direction of the absorbent article. Further, regardless of the shape and size of the perimeter 114a, 114b, or 114c of opening 148, embossed region 112 extends around the multi-layered topsheet 138 in an area that generally frames the opening 148 in the first topsheet layer 106.

Moreover, whether the first topsheet layer opening 148 is defined by perimeter 114a, 114b, or 114c the embossed region 112 can be located about the multi-layered topsheet 138 such that at least a portion of the seal between the first topsheet layer 106 and second topsheet layer 108 discussed above can be generally coextensive with the embossed region 112. For instance, in FIGS. 1-2, the embossed region 112 is generally coextensive with the entire seal between the first topsheet layer 106 and the second topsheet layer 108 because the seal has the same complex, oblong shape as the embossed region 112. Meanwhile, in FIGS. 3-4, 20, and 22, the embossed region 112 is generally coextensive with the part of the seal between the first topsheet layer 106 and the second topsheet layer 108 that extends in the longitudinal (x) direction of the absorbent article.

Additionally, one or more optional embossed regions 110, can be provided near the distal end 102 and/or proximal end 104 of the absorbent article, as shown in FIGS. 1-2, 4-5, and 11. The embossed regions 110 can have a semi-circular shape, although any other suitable shape can be used. The embossed regions 110 can be formed over both the first topsheet layer 106 and second topsheet layer 108 or over just the second topsheet layer 108 depending on the design of the opening 148 in the first topsheet layer 106. For example, in the embodiment of FIGS. 1-2, optional embossed region 110 is only present over the second topsheet layer 108 because the opening 148 in the first topsheet layer 106 defined by perimeter 114a extends beyond the area of the multi-layered topsheet 138 in which embossed region 110 is present. On the other hand, in the embodiment of FIGS. 4-5, embossed region 110 can be present over both the first topsheet layer 106 and the second topsheet layer 108 because the opening 148 in the first topsheet layer 106 defined by perimeter 114b is framed by the area of the multi-layered topsheet 138 in which embossed region 110 is present. Moreover, in another embodiment (not shown), the optional embossed region 110 can be located between embossed region 112 and the distal end 102 and/or proximal end 104 of the absorbent article, such that the embossed region 110 can be formed over both the first topsheet layer 106 and the second topsheet layer 108 even when the opening 148 is defined by larger perimeter 114a rather than smaller perimeter 114b.

Although FIGS. 1-2 and 4-5 only show embossed region 112 and optional embossed region 110 on the multi-layered topsheet 138, any number of embossed regions may be employed in the present invention to direct fluid to a desired location. For instance, in FIG. 11, embossed region 170 is employed to help direct fluid away from the distal end 102 of the topsheet when a distal end topsheet layer opening 164 is employed in an overnight absorbent article. Additionally, in FIGS. 20 and 22, embossed region 180 is employed in an area that extends over the first sub-topsheet layer 116 to provide additional structural support to direct fluid flow towards a central region of the absorbent article 900 or 1000. Further, one or more, in some embodiments two or more, and in some embodiments from two to twenty spaced apart embossed regions can be additionally employed. Regardless of their form, it is typically desired that the embossed regions are arranged in a generally symmetrical manner about a longitudinal centerline $C_L$ and/or transverse centerline $C_T$ of the multi-layered topsheet 138, such as embossed regions 175 shown in FIG. 11. Also, although not required, the embossed regions may be arranged in sets (e.g., pairs) to further enhance aesthetic appeal, as are embossed regions 110 and 180.

In addition to the topsheet layers discussed above, the absorbent article of the present disclosure also includes a first sub-topsheet layer 116. In FIGS. 1-6 and 11-17 and 20-25, for example, a first sub-topsheet layer 116 is positioned between the second topsheet layer 108 of the multi-layered topsheet 138 and the baffle 130 in the z-direction. In other embodiments, such as in absorbent article 800 shown in FIGS. 18-19, the first sub-topsheet layer can be positioned within the multi-layered topsheet 138 between the first topsheet layer 106 and the second topsheet layer 108 in the z-direction. Regardless of its location, the first sub-topsheet layer 116 may be made of a material that is capable of rapidly guiding, transferring and absorbing, in the z-direction, bodily fluid that is delivered to the topsheet at the first topsheet layer opening 148. The first sub-topsheet layer 116 may generally have any shape and/or size desired. In FIGS. 1-6, for instance, the first sub-topsheet layer 116 generally has a simple shape that resembles a racetrack or a rectangle with semi-circular ends and has a length and/or width less than the overall length and/or width of the baffle 130. However, it is to be understood that the first sub-topsheet layer 116 can have a simple rectangular, square, circular, or triangular shape, or a more complex shape having multiple protrusions. For instance, in the absorbent article 900 as shown in FIGS. 20-21, the first sub-topsheet layer 116 has a shape that generally corresponds with the perimeter 114c of the first topsheet layer 106 as discussed above, where a protrusion 184 is present at the first edge 132 and second edge 134 in the transverse (y) direction along the width of the absorbent article 900, giving the first sub-topsheet layer 116 a bulged-looking shape in the transverse (y) direction. This shape of the first sub-topsheet layer 116 can help the three-dimensional layer bend to conform to the wearer's body, thus preventing fluid leakage.

Further, the first sub-topsheet layer 116 can generally have length, width, and thickness dimensions such that it can form a well or cup-like structure that can be used to funnel and hold fluid in a desired location of the absorbent article away from the body-facing surface 144 of the absorbent article. Further, the dimensions of the first sub-topsheet layer can be chosen so that the first sub-topsheet layer is wide enough to capture fluid yet still remain comfortable against the wearer's body. Generally, the length of the first sub-topsheet layer 116 in the longitudinal (x) direction can be from about 20 mm to about 200 mm, such as from about 40 mm to about 175 mm, such as from about 60 mm to about 150 mm. Meanwhile, the width of the first sub-topsheet layer 116 in the transverse (y) direction can be from about 10 mm to about 100 mm, such as from about 15 mm to about 80 mm, such as from about 20 mm to about 60 mm. Further, the first sub-topsheet layer 116 can have a thickness ranging from about 100 micrometers (μm) to about 8 mm, such as from about 500 μm to about 5 mm, such as from about 300 μm to about 3 mm. Regardless of its particular length, width, or thickness, the first sub-topsheet layer 116 can be generally framed by the first topsheet layer opening 148 and can have smaller dimensions than the first topsheet layer opening 148 to help create a funnel-like configuration between the first topsheet layer opening 148 and the first sub-topsheet layer 116, which directs bodily fluids down and toward a desired location in the absorbent article.

Moreover, any of a variety of absorbent article layers can be used as the first sub-topsheet layer 116. For instance, the first sub-topsheet layer 116 can be an additional topsheet layer, a surge layer, a fluid intake layer, or an absorbent core layer. Any materials known in the art can be used in the first sub-topsheet layer, such as the topsheet layer materials discussed in more detail above, and the absorbent core and surge layer materials discussed in more detail below. Further, the first sub-topsheet layer 116 can be synthetic, cellulosic, or a combination of synthetic and cellulosic materials. For example, multifunctional airlaid material such as airlaid cellulosic tissues may be suitable for use in the sub-topsheet layer 116. The airlaid cellulosic tissue may have a basis weight ranging from about 10 gsm to about 300 gsm, and in some embodiments, between about 40 gsm to about 150 gsm. The airlaid tissue may be formed from hardwood and/or softwood fibers. The airlaid tissue has a fine pore structure and provides an excellent wicking capacity, especially for menses.

Additionally, to further enhance the ability of the absorbent article to transfer bodily fluid in the z-direction from its body-facing surface 144 toward any lower layers in the absorbent article as well as to enhance the ability of the first sub-topsheet layer 116 to conform to the wearer's body based on its ability to bend, the first sub-topsheet layer 116 has an opening 150. The opening 150 can be of any suitable shape, such as ovular, circular, rectangular, square, triangular, etc. The opening 150 in the first sub-topsheet layer 116 can serve to further funnel and direct bodily fluid away from the body-facing surface 144 of the absorbent article and towards lower layers of the absorbent article in the z-direction when utilized in conjunction with opening 148 in the first topsheet layer 106, as the opening 150 is smaller than the opening 148 in the first topsheet layer 106 discussed above. The opening 150 can also form a cup or well like structure for holding fluid and preventing its leakage away from a central region of the absorbent article and towards the edges. As such, the opening 150 of the first sub-topsheet layer 116 has a perimeter 118 defined by the first sub-topsheet layer 116 that is substantially surrounded by the first topsheet layer opening 148 and if present, the second topsheet layer opening 162 when viewed from the body-facing surface 144 of the absorbent article. In some instances, the first sub-topsheet layer opening 150 is completely framed by the first topsheet layer opening 148 in the z-direction when viewed from the body-facing surface 144 of the absorbent article. Further, the opening the 148 can be substantially surrounded by embossed region 112 as discussed above. This arrangement creates the aforementioned funnel-like effect to draw bodily fluids away from the body-facing surface 144 of the absorbent article in the z-direction, towards the first sub-topsheet layer 116 or an absorbent layer in the absorbent article.

Generally, the opening 150 can have a length in the longitudinal (x) direction that is from about 15 mm to about 150 mm, such as from about 20 mm to 100 mm, such as from about 30 mm to about 75 mm. The perimeter 118 of the sub-topsheet layer 116 can also form an opening 150 that has a width in the transverse (y) direction that is from about 10 mm to about 80 mm, such as from about 15 mm to about 60 mm, such as from about 20 mm to about 40 mm. The size of the opening 150 allows the first sub-topsheet layer 116 to sufficiently bend to conform to the wearer's body, which can prevent leakage of bodily fluids due to channels that could be created in the absorbent article upon the introduction of compressive forces. It is also desirable that the opening 150 be large enough for a consumer to easily view and place it directly under a vaginal opening so that it is located underneath the portion of the body-facing surface of the absorbent article having primary contact with bodily fluids. To further assist in the proper placement of the absorbent article, the first sub-topsheet layer 116 can thus be constructed of a colored material or it can be dyed or printed a color that is distinct from the other layers of the absorbent article 100 or 200 and visible through at least the first and second topsheet layers or any other layers disposed above the first sub-topsheet layer 116 in the z-direction when viewed from the body-facing surface 144 of the absorbent article. This can provide an aesthetically pleasing appearance to the absorbent article and can also help the wearer position the first sub-topsheet layer 116 in the appropriate location by providing a visual cue as to the proper positioning of the absorbent article.

Furthermore, in the absorbent article of the present disclosure, it is to be understood that the first sub-topsheet layer 116 can have a thickness in the ranges discussed above that is substantial enough to create a three-dimensional, hump-like configuration in the absorbent article to further enhance the funneling effect of the arrangement of the various layers and openings in the absorbent article, as shown in FIGS. 14-17 and 28-29. In particular, a cross-sectional view of the width of absorbent article 600 in the transverse (y) direction is shown before (FIG. 14) and after assembly (FIG. 15). In absorbent article 600, the first topsheet layer 106 has an opening 148, and the second topsheet layer 108 has no opening such that the second topsheet layer 108 remains exposed at the first topsheet layer opening 148. Further, the first sub-topsheet layer 116 has a first sub-topsheet layer opening 150 that is smaller than the first topsheet layer opening 148 such that the first sub-topsheet layer opening 150 is substantially surrounded by the first topsheet layer opening 148 if viewed from the body-facing surface of the absorbent article in the z-direction. The first sub-topsheet layer 116 also has a width and a length (not shown) that is generally the same size or smaller than the width and the length of the opening 148 in the first topsheet layer 108. Thus, the first sub-topsheet layer 116 is substantially surrounded or framed by the perimeter of the first topsheet layer opening 148 in the multi-layered topsheet when viewing the absorbent article from its body-facing surface. This allows the first sub-topsheet layer 116 to be comfortable against the wearer's body and also allows it to conform to the wearer's body more easily. Further, the thickness of the sub-topsheet layer 116 results in the first sub-topsheet layer 116 and the sub-topsheet opening 150 forming a raised, well-like configuration in the center of the absorbent article 600 above the absorbent core 128, which can enhance the ability of the absorbent article of the present disclosure to hold fluids in a central location of the absorbent article to prevent leakage. The prominence of such a first sub-topsheet layer 116 also allows the user to have a strong visual cue for proper placement of the absorbent article.

In yet another embodiment, as shown in FIGS. 28 and 29, an absorbent article 1200 can be formed where the first topsheet layer 106 has an opening 148 and the second topsheet layer 108 has no opening such that the second topsheet layer 108 remains exposed at the first topsheet layer opening 148. Further, the first sub-topsheet layer 116 can have a first sub-topsheet layer opening 150 that has a larger perimeter (i.e., has a greater length in the longitudinal (x) direction and a greater width in the transverse (y) direction) than the perimeter that defines the first topsheet layer opening 148 such that the entirety of the first sub-topsheet layer opening 150 is not contained within the perimeter of the first topsheet layer opening 148 when viewed from the body-facing surface of the absorbent article in the z-direction. Further, the first sub-topsheet layer 116 can have a width and a length (not shown) that is generally larger than the width and the length of the opening 148 in the first topsheet layer 108. Thus, the first sub-topsheet layer 116 can extend past the perimeter of the first topsheet layer opening 148 in the multi-layered topsheet when viewing the absorbent article from its body-facing surface. The smaller first topsheet layer opening in absorbent article 1200 can allow the sub-topsheet layer 116 to receive fluid at a more centralized location in the absorbent article, after which the fluid can be directed to a desired location in the absorbent article, such as at the sub-topsheet layer 116 or absorbent core 128.

In another embodiment, as shown in FIGS. 16-17, an absorbent article 700 can be formed such that it has multiple openings in the multi-layered topsheet to further enhance the ability of the absorbent article to draw fluid away from the wearer's body and towards a centralized location or well in the absorbent article. For instance, in FIGS. 16 and 17, a cross-sectional view of absorbent article 700 in the transverse (y) direction is shown before (FIG. 16) and after assembly (FIG. 17). In absorbent article 700, the first topsheet layer 106 has an opening 148, the second topsheet layer 108 has an opening 162. The second topsheet layer opening 162 is smaller than the first topsheet layer 106 such that the perimeter of second topsheet layer opening 162 is surrounded by the perimeter of the first topsheet layer opening 148 when viewed from the body-facing surface of the absorbent article in the z-direction. However, it is also to be understood that the second topsheet opening 162 can be larger than the first topsheet layer opening 148. Regardless of which of the topsheet layer openings is larger, a third topsheet layer 182 without an opening is disposed beneath the second topsheet layer 108 in the z-direction and is positioned over a first sub-topsheet layer 116. The sub-topsheet layer opening 150 is generally the same size or smaller than the width of the largest of the topsheet layer openings. Further, in FIGS. 16 and 17, it is to be understood that the width and length (not shown) of the first sub-topsheet layer 116 itself generally allows the entire sub-topsheet layer 116 to be substantially surrounded or framed by the perimeter of the largest opening in the multi-layered topsheet when viewing the absorbent article from its body-facing surface. The combination of the thickness of the first sub-topsheet layer 116 and the length and width of the sub-topsheet layer 116 result in the first sub-topsheet layer 116 and the sub-topsheet opening 150 forming a raised, well-like configuration in the center of the absorbent article 700, which can further enhance the ability of the absorbent article of the present disclosure to hold fluids in a central location of the absorbent article to prevent leakage. Again, as described above in reference to FIGS. 14 and 15, the prominence of such a first sub-topsheet layer 116 also allows the user to have a strong visual cue for proper placement of the absorbent article.

Although FIGS. 14-17 show that the first sub-topsheet layer 116 is positioned below both the first topsheet layer 106 and the second topsheet layer 108, it is to be understood that in some embodiments, the first sub-topsheet layer 116 can be positioned between the first topsheet layer 106 and the second topsheet layer 108 such that it is placed between different layers of the multi-layered topsheet. This particular embodiment is shown in FIGS. 18 and 19, where a cross-sectional view of absorbent article 800 in the transverse (y) direction is shown before (FIG. 18) and after assembly (FIG. 19).

Further, it is also to be understood that more than one sub-topsheet layer can be present in the absorbent article to further provide structural support to the absorbent article, allow the absorbent article to bend and conform to the user's body, provide a funneling effect, and to hold fluid in a well in a desired location of the absorbent article. For instance, in FIGS. 22-27, in addition to having a first sub-topsheet layer 116, the absorbent articles 1000, 1100, and 1200 also include a second sub-topsheet layer 174 that is at least partially visible from the body-facing surface 144 of the absorbent article in the z-direction. The second sub-topsheet layer 174 shape can be a complex shape that corresponds with a perimeter 114c of the first topsheet layer 106, which has a protrusion 184 present at the first edge 132 and second edge 134 of the absorbent article in the transverse (y) direction, giving the second sub-topsheet layer 174 a bulged looking shape in the transverse (y) direction. Meanwhile, the first sub-topsheet layer 116 can have a simple shape that resembles a racetrack or a rectangle having semi-circular ends. The shape of the second sub-topsheet layer 174 can help the three-dimensional layer bend to conform to the wearer's body, thus preventing fluid leakage. The bulges or protrusions in the second sub-topsheet layer 174 extend beyond the periphery of the first sub-topsheet layer 116 in the transverse (y) direction when viewed from the body-facing surface 144 of the absorbent article. Thus, when two sub-topsheet layers are present, the perimeter 114c of the opening 150 in the first topsheet layer 106 generally corresponds with the shape of the larger sub-topsheet layer, which is, in this instance, the second sub-topsheet layer 174 because of its visible bulges in the transverse (y) direction. Additionally, as shown in the transverse (y) direction cross-sectional views of an unassembled (FIG. 24) and assembled (FIG. 25) absorbent article 1100, the first sub-topsheet layer 116 and second sub-topsheet layer 174 can be positioned below the second topsheet layer 108 in the z-direction such that the second sub-topsheet layer 174 is below the first sub-topsheet layer 116 with no additional absorbent article layers separating the first sub-topsheet layer 116 and the second sub-topsheet layer 174. However, in other embodiments, the second topsheet layer 108 can be positioned between the first sub-topsheet layer 116 and the second sub-topsheet layer 174 in the z-direction, as shown in FIGS. 26 and 27, which show transverse (y) direction cross-sectional views of an unassembled (FIG. 26) and assembled (FIG. 27) absorbent article 1200.

Like the first sub-topsheet layer 116, which has an opening 150 defined by a perimeter 118, the second sub-topsheet layer 174 can also have an opening. As shown in FIGS. 23, 24, and 25, the openings 150 and 178 can generally be the same size such that the first sub-topsheet layer 116 and the second sub-topsheet layer 174 create a uniformly-dimensioned well in absorbent articles 1000 and 1100 for holding fluid in a desired location beneath the multi-layered topsheet. However, in other embodiments, such as the embodiment of absorbent article 1200 shown in FIGS. 26 and 27, the second sub-topsheet layer 174 can have an opening 178 defined by perimeter 176 that is slightly smaller than the opening 150 of first sub-topsheet layer 116. Thus, the opening 178 of the second sub-topsheet layer 174 can be substantially surrounded or framed by the opening 150 of the first sub-topsheet layer 116 when viewed from the body-facing surface of the absorbent article. This configuration can enhance the funneling effect of the absorbent article to draw fluids away from the body-facing surface and towards a desired location in the absorbent article below the multi-layered topsheet in the z-direction to prevent fluid leakage.

Moreover, in some embodiments, such as the embodiment shown in FIG. 11, the absorbent article can include a distal end sub-topsheet layer 168 that is separate from but in the same plane as the first sub-topsheet layer 116. The distal end sub-topsheet layer 168 can include any of the materials discussed above for the first sub-topsheet layer 116 and is situated beneath the distal end first topsheet layer opening 164, as defined by perimeter 166. The distal end sub-topsheet layer 168 is utilized in an overnight absorbent article to prevent leakage at the distal end 102 of the absorbent article during overnight use, which could stain clothing or bedding. The distal end sub-topsheet layer 168 can be of any shape, such as a complex shape or a simple shape, such as the ovular shape shown in FIG. 11. Regardless of the shape, the distal end sub-topsheet layer 168 is smaller than the distal end first topsheet layer opening 164 having perimeter 166 so as to create a funnel-like effect for drawing fluid down in the z-direction to an absorbent layer of the absorbent article to help prevent leakage at the distal end 102.

Furthermore, in the illustrated embodiments, in addition to the layers discussed above, the absorbent article also includes a liquid impermeable baffle 130. The baffle 130 is generally liquid impermeable and defines a garment-facing surface 142 of the absorbent article. The baffle 130 may permit the passage of air or vapor out of the absorbent article, while still blocking the passage of liquids. Any liquid impermeable material may generally be utilized to form the baffle 130. For example, one suitable material that may be utilized is a microporous polymeric-filled film, such as a polyethylene-based or polypropylene-based film. In particular embodiments, a polyethylene film is utilized that has a thickness in the range of from about 5 μm to about 150 μm, such as from about 10 μm to about 75 μm. A specific example of a baffle material is a polyethylene film such as that used in KOTEX® pantiliners and obtainable from Pliant Corporation, Schaumburg, Ill., USA.

The absorbent article can also include an absorbent core 128 that is disposed between the baffle 130 and the multi-layered topsheet 138, an optional first surge layer 120 that can be positioned between the multi-layered topsheet 138 and the first sub-topsheet layer 116, and an optional second surge layer 126 that can be positioned between the first sub-topsheet layer 116 and the absorbent core 128. Each of these features is discussed in more detail below.

As indicated above, an absorbent core 128 can be positioned between the multi-layered topsheet 138 and the baffle 130. The absorbent core 128 can provide additional capacity to absorb and retain bodily exudates in addition to the first sub-topsheet layer 116 performing this function. Additionally, the absorbent core 128 may be formed from a variety of different materials and contain any number of desired layers. For example, the core 128 typically includes one or more layers (e.g., two layers) of an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In a particular embodiment, the absorbent web material includes a matrix of cellulosic fluff, and may also include superabsorbent material. The cellulosic fluff may comprise a blend of wood pulp fluff. One preferred type of fluff is identified with the trade designation NB 416, available from Weyerhaeuser Corp., and is a bleached, highly absorbent wood pulp containing primarily soft wood fibers.

If desired, the absorbent core 128 can include an optional amount of superabsorbent materials. Examples of suitable superabsorbent materials include poly(acrylic acid) and poly(methacrylic acid), poly(acrylamides), poly(vinyl ethers), maleic anhydride copolymers with vinyl ethers and α-olefins, poly(vinyl pyrrolidone), poly(vinylmorpholinone), poly(vinyl alcohol), and salts and copolymers thereof. Other superabsorbent materials include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum, and so forth. Mixtures of natural and wholly or partially synthetic superabsorbent polymers may also be useful in the present invention. The superabsorbent material can be present in the absorbent core 128 in any amount as desired.

Regardless of the combination of absorbent materials used in the absorbent core 128, the absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. A coform nonwoven material may also be employed. Methods and apparatus for carrying out such techniques are well known in the art.

In addition to the multi-layered topsheet 138, the first sub-topsheet layer 116, the absorbent core 128, and the baffle 130, the absorbent article of the present disclosure can also contain other additional layers as are known in the art. For instance, the absorbent article of the present disclosure may also contain one or more surge layers. Generally, surge layers 120 and 126, as shown in FIGS. 3, 6, 12, and 13, can be constructed of any woven or nonwoven material that is easily penetrated by bodily exudates. The surge layers help to absorb, decelerate, and diffuse surges or gushes of liquid that may be rapidly introduced into the absorbent article 100 or 200. The surge layers 120 and 126 can rapidly accept and temporarily hold the liquid prior to releasing the liquid into, for instance, the absorbent core 128 or any other layer of the absorbent article. The first surge layer 120 can be located between the second topsheet layer 108 and the first sub-topsheet layer 116, while the second surge layer 126 can be located between the first sub-topsheet layer 116 and the baffle 130, such as between the first sub-topsheet layer 116 and the absorbent core 128. Various woven fabrics and nonwoven webs can be used to construct the surge layers 120 and 126. For example, the surge layers may comprise a nonwoven fabric layer composed of a meltblown or spunbond web of polyolefin or polyester filaments. Such nonwoven fabric layers may include conjugate, biconstituent and homopolymer fibers of staple or other lengths and mixtures of such fibers with other types of fibers. The surge layers 120 and 126 also can be a bonded carded web or an airlaid web composed of natural and/or synthetic fibers. The bonded carded web may, for example, be a powder bonded carded web, an infrared bonded carded web, or a through-air bonded carded web. The bonded carded webs can optionally include a mixture or blend of different fibers. The surge layers typically have a basis weight of less than about 100 gsm, and in some embodiments, from about 10 gsm to about 40 gsm.

If desired, one or more of the surge layers can be dyed or printed with a pattern that is visible from the body-facing surface 144 of the absorbent article to highlight the sub-topsheet layer opening 150 and aid in the proper placement of the absorbent article. For instance, as shown in FIGS. 1-6 and 12-13, the second surge layer 126 can be printed with a pattern 122 with, for instance, a wax jet ink. Any suitable pattern can be printed onto the surge layer, although a pattern of circular dots is shown in FIGS. 1-6 and 12-13. The pattern 122 can correspond to an area framed by the opening 150 in the first sub-topsheet layer 116 and the opening 148 in the first topsheet layer 106 so that the pattern 122 is visible from the body-facing surface 144 of the absorbent article. The pattern 122 can enhance the aesthetic appearance of the absorbent article and can also assist the wearer in positioning the absorbent article in the appropriate location on a garment by providing a visual cue. Although surge layers have been discussed in detail above, it is to be understood that instead of or in addition to the surge layers described, other layers can be utilized in the absorbent article, such as intake layers, transfer layers, or distribution layers, and these layers and the surge layers can be colored, shaded, or patterned to provide a visual cue to the wearer for the proper placement of the absorbent article. Further, when numerous layers are utilized, each layer can have a distinct color, shading, or pattern to further aid the wearer in placing the absorbent article in the proper location.

It is to be understood that regardless of the layers present in the absorbent article, the various layers of the absorbent article may be maintained in secured relation with each other by bonding all or a portion of the adjacent surfaces to one another. A variety of bonding mechanisms known to one of skill in the art may be utilized to achieve any such secured relation. Examples of such mechanisms include, but are not limited to, the application of adhesives or embossing in a variety of patterns between the two adjoining surfaces, entangling at least portions of one surface with portions of the adjacent surface, or fusing at least portions of one surface to portions of the adjacent surface (e.g., ultrasonically fusing).

For example, the multi-layered topsheet 138 may be bonded to the base baffle 130 using any pattern desired, such as continuous or discontinuous (e.g., toothed, stepped, dots, etc.). Further, depending on the size and geometry of the first topsheet layer 106 and the second topsheet layer 108 and the location of the bonding, either the first topsheet layer 106 or the second topsheet layer 108 may come in direct contact with the baffle 130. For instance, if the peripheral margins of the second topsheet layer 108 extend to the peripheral margins of the first topsheet layer 108, and the multi-layered topsheet 138 is bonded to the baffle 130 about the periphery of the absorbent article, the second topsheet layer 108 will be in direct contact with the baffle 130. On the other hand, if the overall dimensions of the second topsheet layer 108 are smaller than that of the first topsheet layer 106, then the first topsheet layer 106 may come in direct contact with the baffle 130. Further, adhesives or other types of bonding can be used to bond together the absorbent core 128 and baffle 130, or any of the other optional layers present in the absorbent article.

In addition to the various layers discussed above, the various embodiments of absorbent article of the present disclosure may also include laterally extending wing portions 136 that may be integrally connected to side regions along the intermediate portion of the article. For example, the wing portions 136 may be separately provided members that are subsequently attached or otherwise operatively joined to the intermediate portion of the article. In other configurations, the wing portions may be unitarily formed with one or more components of the article. As representatively shown in FIG. 1, for example, either or both wing portions 136 may be formed from a corresponding, operative extension of the material employed to form the first topsheet layer 106. Alternatively, either or both wing portions 136 may be formed from a corresponding, operative extension of the material employed to form the baffle 130, or formed from a corresponding, operative combination of the multi-layered topsheet 138 and baffle 130 materials.

Further, if desired, various structural members may also be employed to further enhance the three-dimensional topography of the absorbent article. Fluidic guides may also be employed in the present invention to assist in leakage prevention, such as those described in U.S. Pat. No. 5,614,295 to Quincy, III, et at, U.S. Pat. No. 7,388,123 to Cowell, et al., U.S. Pat. No. 5,912,194 to Everhart, et al., and U.S. Pat. No. 4,892,534 to Datta, et al., which are incorporated herein in their entireties by reference thereto. Such fluidic guides may be employed in the center and/or periphery of the article as desired.

Further, while not shown, the garment-facing surface 142 of the baffle 130 of any of the above-described absorbent articles may include an adhesive that has been applied to the garment-facing surface of the baffle. The adhesive can be utilized to attach the absorbent article to a garment such as underwear. In addition, a release liner or peel strip may be applied over the adhesive to prevent adhesive contamination until the absorbent article is ready to be used. The adhesive may be composed of any suitable adhesive. For example, the adhesive may be a pressure-sensitive adhesive such as EASYMELT 34-5602, available from National Starch and Chemical Company. Examples of suitable peel strips include a silicone coated Kraft paper, a silicone coated film, or the like. Other release coatings include coatings containing polytetrafluoroethylene.

As a result of the combination of features employed in the present invention, an absorbent article may thus be formed that is comfortable to wear and provides a high level of dryness, while also exhibiting a reduced likelihood of leakage during use. This may be evident throughout the entire use of the article, including upon an initial insult of a fluid and subsequently when the article has already absorbed a certain amount of fluid.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article that extends in a plane defined by a longitudinal direction and a transverse direction, wherein the article comprises:
   a liquid permeable multi-layered topsheet having a length in the longitudinal direction, a width in the transverse direction, a longitudinal centerline, and a transverse centerline, wherein the multi-layered topsheet defines a body-facing surface of the absorbent article, the multi-layered topsheet comprising at least a first topsheet layer disposed above a second topsheet layer, wherein the first topsheet layer defines a first opening having a first perimeter, wherein the first topsheet layer and the second topsheet layer are joined by a seal, and further wherein the multi-layered topsheet extends in the longitudinal direction to define a distal end and an opposing proximal end of the absorbent article and in the transverse direction to define a first edge and an opposing second edge of the absorbent article;
   a liquid impermeable baffle, wherein the baffle defines a garment-facing surface of the absorbent article;
   a first sub-topsheet layer positioned between the second topsheet layer and the baffle, wherein the first sub-topsheet layer defines a second opening having a second perimeter, wherein the first perimeter surrounds the second perimeter; and
   a second sub-topsheet layer positioned between the first sub-topsheet layer and the baffle, wherein the second sub-topsheet layer has a shape that includes a first bulge facing the first edge in the transverse direction and a second bulge facing the second edge in the transverse direction, wherein the first bulge and the second bulge are visible from the body-facing surface of the absorbent article, and further wherein the second sub-topsheet layer defines a third opening having a third perimeter.

2. The absorbent article of claim 1, wherein the first opening has an ovular shape.

3. The absorbent article of claim 1, wherein the first opening has an oblong shape, wherein the first perimeter is defined by one or more protrusions in the longitudinal direction and one or more protrusions in the transverse direction.

4. The absorbent article of claim 1, wherein the multi-layered topsheet comprises an embossed region, wherein the embossed region surrounds the first opening.

5. The absorbent article of claim 4, wherein the embossed region has a shape that corresponds with the perimeter of the first opening.

6. The absorbent article of claim 1, wherein the first opening is in alignment with the longitudinal centerline.

7. The absorbent article of claim 6, wherein the first opening is in alignment with the transverse centerline.

8. The absorbent article of claim 6, wherein the first opening is located towards the distal end or proximal end of the first topsheet layer.

9. The absorbent article of claim 1, wherein the first opening has a length that is from about 15% to about 80% of the length of the first topsheet layer.

10. The absorbent article of claim 1, wherein the first opening has a width that is from 20% to about 80% of the width of the first topsheet layer.

11. The absorbent article of claim 1, wherein the seal is continuous.

12. The absorbent article of claim 1, wherein the seal is formed by an adhesive bond, a pressure bond, a thermal bond, an ultrasonic bond, or a combination thereof.

13. The absorbent article of claim 4, wherein at least a portion of the seal is coextensive with the embossed region.

14. The absorbent article of claim 1, wherein the first topsheet layer is disposed above the second topsheet layer at the distal end, the proximal end, the first edge, and the second edge of the absorbent article.

15. The absorbent article of claim 1, wherein at least one printed graphic is visible from the body-facing surface of the absorbent article along each of the distal end, proximal end, first edge, and second edge of the absorbent article.

16. The absorbent article of claim 1, wherein the length of the second topsheet layer ranges from about 30% to about 100% of the length of the first topsheet layer.

17. The absorbent article of claim 1, wherein the width of the second topsheet layer ranges from about 10% to about 100% of the width of the first topsheet layer.

18. The absorbent article of claim 1, wherein a first liquid permeable layer is positioned between the second topsheet layer and the first sub-topsheet layer.

19. The absorbent article of claim 1, wherein a second liquid permeable layer is positioned between the first sub-topsheet layer and the baffle, wherein a pattern is printed on the second liquid permeable layer such that the pattern is visible from the body-facing surface of the absorbent article.

20. The absorbent article of claim 1, wherein a portion of the second topsheet layer is exposed beneath the first opening, further wherein the seal corresponds with the first perimeter.

21. The absorbent article of claim 1, wherein the second topsheet layer defines a fourth opening having a fourth perimeter and the absorbent article further comprises a third topsheet layer, wherein the third topsheet layer is disposed between the second topsheet layer and the first sub-topsheet layer.

22. The absorbent article of claim 21, wherein the first perimeter surrounds the fourth perimeter, further wherein the seal corresponds with the first perimeter.

23. The absorbent article of claim 21, wherein the fourth perimeter surrounds the first perimeter, further wherein the seal corresponds with the fourth perimeter.

24. The absorbent article of claim 1, wherein an absorbent core is disposed between the first sub-topsheet layer and the baffle.

25. The absorbent article of claim 1, further comprising a distal end sub-topsheet layer positioned at the distal end of the absorbent article between the second topsheet layer and the baffle, wherein the first topsheet layer defines a fifth opening having a fifth perimeter, wherein the distal end sub-topsheet layer exists in the same plane as the first sub-topsheet layer and has an ovular shape.

26. An absorbent article that extends in a plane defined by a longitudinal direction and a transverse direction, wherein the absorbent article comprises, in sequential order from a body-facing surface to a garment facing surface of the absorbent article, the following:
   a liquid permeable multi-layered topsheet, wherein the liquid permeable multi-layered topsheet comprises a first topsheet layer disposed above a second topsheet layer, wherein the first topsheet layer defines a first opening having a first perimeter, wherein the first topsheet layer and the second topsheet layer are joined by a seal, and further wherein the multi-layered topsheet extends in the longitudinal direction to define a distal end and an opposing proximal end of the absorbent article and in the transverse direction to define a first edge and an opposing second edge of the absorbent article, wherein at least one printed graphic is present on the first topsheet layer and visible from the body-facing surface of the absorbent article along each of the distal end, proximal end, first edge, and second edge of the absorbent article;
a first liquid permeable surge layer;
a first sub-topsheet layer, wherein the first sub-topsheet layer defines a second opening having a second perimeter, wherein the first perimeter surrounds the second perimeter;
a second liquid permeable surge layer, wherein a pattern is printed on the second liquid permeable surge layer such that the pattern is visible from the body-facing surface of the absorbent article;
an absorbent core;
a liquid impermeable baffle; and
a second sub-topsheet layer positioned between the first sub-topsheet layer and the baffle, wherein the second sub-topsheet layer has a shape that includes a first bulge facing the first edge in the transverse direction and a second bulge facing the second edge in the transverse direction, wherein the first bulge and the second bulge are visible from the body-facing surface of the absorbent article, and further wherein the second sub-topsheet layer defines a third opening having a third perimeter.

* * * * *